United States Patent
Hoganson et al.

(10) Patent No.: US 9,162,039 B2
(45) Date of Patent: Oct. 20, 2015

(54) FLOW DIRECTED GUIDEWIRE

(76) Inventors: David M. Hoganson, Boston, MA (US);
Ravi K. Veeraswamy, Atlanta, GA (US)

( * ) Notice: Subject to any disclaimer, the term of this patent is extended or adjusted under 35 U.S.C. 154(b) by 2089 days.

(21) Appl. No.: 11/465,668

(22) Filed: Aug. 18, 2006

(65) Prior Publication Data
US 2008/0097402 A1    Apr. 24, 2008

(51) Int. Cl.
A61M 25/09    (2006.01)
A61M 25/01    (2006.01)
A61B 5/00     (2006.01)
A61B 17/12    (2006.01)

(52) U.S. Cl.
CPC ........... *A61M 25/09* (2013.01); *A61M 25/0125* (2013.01); *A61B 5/6851* (2013.01); *A61B 17/12022* (2013.01); *A61M 2025/09175* (2013.01)

(58) Field of Classification Search
CPC .......... A61B 5/6851; A61B 17/12022; A61M 25/0125; A61M 25/09; A61M 2025/09175
USPC .................. 606/191; 604/528, 509, 103, 245; 600/156, 585
See application file for complete search history.

(56) References Cited

U.S. PATENT DOCUMENTS

| | | | |
|---|---|---|---|
| 4,024,873 A | 5/1977 | Antoshkiw et al. | |
| 4,029,104 A | 6/1977 | Kerber | |
| 4,721,118 A * | 1/1988 | Harris | ............................ 607/128 |
| 4,723,549 A | 2/1988 | Wholey et al. | |
| 4,983,169 A | 1/1991 | Furukawa | |
| 5,053,008 A | 10/1991 | Bajaj | |
| 5,160,342 A | 11/1992 | Reger et al. | |
| 5,499,973 A | 3/1996 | Saab | |
| 5,538,512 A | 7/1996 | Zenzon et al. | |
| 5,637,086 A | 6/1997 | Ferguson et al. | |
| 5,730,733 A | 3/1998 | Mortier et al. | |
| 5,899,890 A | 5/1999 | Chiang et al. | |
| 5,906,618 A | 5/1999 | Larson, III | |
| 5,911,715 A | 6/1999 | Berg et al. | |
| 5,947,939 A | 9/1999 | Mortier et al. | |
| 6,083,222 A | 7/2000 | Klein et al. | |
| 6,086,599 A | 7/2000 | Lee et al. | |
| 6,099,558 A | 8/2000 | White et al. | |
| 6,110,164 A | 8/2000 | Vidlund | |
| 6,126,650 A | 10/2000 | Martinez et al. | |
| 6,171,796 B1 | 1/2001 | An et al. | |
| 6,179,851 B1 | 1/2001 | Barbut | |
| 6,193,705 B1 | 2/2001 | Mortier et al. | |

(Continued)

FOREIGN PATENT DOCUMENTS

EP    1 266 670 A    12/2002
WO    WO 98/41163 A    9/1998

(Continued)

*Primary Examiner* — Devin Henson
(74) *Attorney, Agent, or Firm* — Jeffrey R. Ramberg

(57) ABSTRACT

A device for accessing a vessel, duct or lumen, comprising a guidewire having a proximal end and a distal end, and at least one projection that extends from said guidewire at or near the distal end of the guidewire. When the guidewire is placed into the vessel, duct or lumen containing a flowing fluid, the drag on the guidewire is greater when the fluid is flowing from the proximal to distal end of the guidewire than it is when it is flowing distally-to-proximally, thereby helping to direct the guidewire. The device is particularly useful in crossing a narrowing in the vessel, duct or lumen, such as may occur in blood vessels containing a stenosis, such as due to atherosclerosis.

41 Claims, 22 Drawing Sheets

(56) References Cited

U.S. PATENT DOCUMENTS

| | | | |
|---|---|---|---|
| 6,203,561 B1 * | 3/2001 | Ramee et al. | 606/200 |
| 6,221,059 B1 | 4/2001 | Chiang | |
| 6,368,338 B1 | 4/2002 | Konya et al. | |
| 6,425,909 B1 * | 7/2002 | Dieck et al. | 606/200 |
| 6,491,671 B1 * | 12/2002 | Larson et al. | 604/264 |
| 6,511,492 B1 | 1/2003 | Rosenbluth et al. | |
| 6,514,237 B1 | 2/2003 | Masela | |
| 6,524,299 B1 | 2/2003 | Tran et al. | |
| 6,591,472 B1 | 7/2003 | Noone et al. | |
| 6,605,056 B2 | 8/2003 | Eidenschink et al. | |
| 6,635,068 B1 | 10/2003 | Dubrul et al. | |
| 6,652,505 B1 | 11/2003 | Tsugita | |
| 6,669,721 B1 | 12/2003 | Bose et al. | |
| 6,716,231 B1 | 4/2004 | Rafiee et al. | |
| 6,726,700 B1 | 4/2004 | Levine | |
| 6,773,448 B2 * | 8/2004 | Kusleika et al. | 606/200 |
| 6,808,498 B2 | 10/2004 | Laroya et al. | |
| 6,976,991 B2 | 12/2005 | Hebert et al. | |
| 7,001,407 B2 * | 2/2006 | Hansen et al. | 606/200 |
| 7,044,958 B2 | 5/2006 | Douk et al. | |
| 7,166,120 B2 * | 1/2007 | Kusleika | 606/191 |
| 7,320,697 B2 * | 1/2008 | Demond et al. | 606/200 |
| 8,221,446 B2 * | 7/2012 | Pal et al. | 606/200 |
| 2003/0040736 A1 | 2/2003 | Stevens et al. | |
| 2004/0153118 A1 * | 8/2004 | Clubb et al. | 606/200 |
| 2004/0236395 A1 | 11/2004 | Iaizzo et al. | |
| 2005/0113862 A1 * | 5/2005 | Besselink et al. | 606/200 |
| 2005/0228417 A1 * | 10/2005 | Teitelbaum et al. | 606/159 |
| 2006/0161229 A1 * | 7/2006 | Laufer | 607/96 |

FOREIGN PATENT DOCUMENTS

| | | |
|---|---|---|
| WO | WO 00/13736 A | 3/2000 |
| WO | WO 03/047675 A | 6/2003 |
| WO | WO 2005/105191 A | 11/2005 |

* cited by examiner

FLOW DIRECTED GUIDEWIRE

BACKGROUND OF THE INVENTION

1. Field of the Invention

The instant invention pertains to flow-directed guidewires and catheters, and in particular, to flow-directed guidewires useful for traversing a stenosis in a blood vessel.

2. Discussion of Related Art

Despite advances in guidewire and catheter technology, high-grade stenoses in the coronary or peripheral vasculature continue to pose a considerable challenge. Even experienced interventionalists can expend significant time, effort and resources in crossing these lesions. Furthermore, multiple, failed attempts at traversing a lesion can increase the risk of distal embolization which may have significant implications in some vascular beds. Numerous modifications to guidewires have attempted to increase the efficiency of crossing stenotic areas. For example, hydrophilic coatings, varying degrees and lengths of "floppiness", and different shapes on the wire tip have all been utilized to facilitate this process. The very existence of multiple products speaks to the lack of universal efficacy of any single design. The central issue is that the tip of the wire must enter the opening of the stenosis. This opening is usually eccentric and difficult to locate efficiently. In effect, trial and error is the current method of choice to get the tip of the wire into the stenosis and may involve multiple attempts. It is obvious that a guidewire that will quickly and atraumatically cross lesions will be of tremendous benefit to both the interventionalist and to the patient.

In addition to crossing lesions in peripheral vascular beds, endovascular technology is being increasingly applied to treat carotid artery lesions (Roubin et al). An integral step in this procedure is to gain wire-access to the appropriate carotid artery via the aortic arch and advance a sheath over this wire into the common carotid artery. The aortic arch anatomy can be very difficult to navigate and the aorta and carotid orifice can be heavily diseased. It has been established that distal embolization due to excessive instrumentation in the aortic arch can lead to cerebral events during carotid stenting procedures (Coggia et al, Macleod et al). Innumerable catheters have been developed to help engage the carotid or innominate orifice but this can be difficult, dangerous and time-consuming. Again, a device that will efficiently and safely allow a wire to be placed into a carotid artery would be useful to clinicians and beneficial to patients.

Flow-directed catheters have been available for decades. These catheters have found application in neuro-interventional radiology. In general they are simply very floppy or flexible tubes of small diameter which will small enough and flexible enough to be effected by fluid velocity and thus are directed through vessels into the branches with the highest flow. Multiple variations of this concept have been disclosed and claimed in the following U.S. patents: U.S. Pat. No. 6,524,299 (Tran et al.); U.S. Pat. No. 5,336,205 (Zenzen et al.); U.S. Pat. No. 5,538,512 (Zenzon et al.); U.S. Pat. No. 6,193,705 (Mortier et al.); U.S. Pat. No. 5,947,939 (Mortier et al.); U.S. Pat. No. 5,730,733 (Mortier et al.); U.S. Pat. No. 6,221,059 (Chiang et al.); U.S. Pat. No. 5,899,890 (Chiang et al.); U.S. Pat. No. 6,083,222 (Klein et al.); U.S. Pat. No. 4,983,169 (Furukawa); U.S. Pat. No. 5,499,973 (Saab); and U.S. Pat. No. 5,911,715 (Berg).

Inflated balloons have been conceived as a method to utilize the flow within a vessel to direct a catheter. In U.S. Pat. No. 4,029,104 (Kerber) an inflatable leaking balloon is described as a tool for using the flow in a vessel to direct the balloon in the direction of flow and also to provide a means of local drug delivery through the small holes in the balloon. Another example of a balloon catheter directed by flow is U.S. Pat. No. 4,024,873 (Antoshkiw et al.).

U.S. Pat. No. 5,906,618 (Larson) describes a catheter with a deployable parachute attached to the distal tip. The parachute may be guided by the flow within a vessel or by fluid injected through the catheter. A guidewire may be advanced through the lumen of the catheter to provide further direction of the catheter into a desired vessel branch. U.S. Pat. No. 6,491,671 (Larson et al.) describes a catheter with a catheter which is directed within a vessel by a wing shaped structure which provides hemodynamic lift in the presence of flow. This wing shaped structure is utilized to guide the tip of the catheter into a desired vessel branch.

U.S. Pat. No. 6,635,068 (Dubrul et al.) describes a catheter with an expandable wire mesh at the distal tip. The wire mesh may be expanded by the operator and flow within the vessel may direct the wire mesh and catheter. The wire mesh may also be used as an occlusion device.

In U.S. Pat. No. 6,726,700 (Levine) and U.S. Pat. No. 6,976,991 (Hebert et al.) describe a catheter with an inflatable balloon which may assist in guiding the catheter through tortuous vasculature. The catheter may include a flexible region where the tip of the catheter may be effectively steered by placing a bent wire within the catheter to bend the catheter in this flexible region so that by torquing the catheter with advancement it may be directed into a desired portion of a vessel such as an aneurysm.

Since 1991, flow-directed catheters have been commercially available. However, their use has been limited by the lack of ability to maneuver in tortuous vascular anatomy and cross stenoses. Typically, a guidewire is required to navigate these anatomic hurdles. The distinction is crucial as catheters are limited by size, structure, rigidity, floppiness or other properties in their design and are not useful for the aforementioned situations. The use of a wire with a floppy tip that can also exploit the flow-dynamics inherent to the vascular system will overcome these limitations

SUMMARY OF THE INVENTION

In accordance with one preferred embodiment of the invention, a flexible, collapsible member is mounted on a guidewire or catheter. This collapsible member, when in the expanded position imparts drag forces to the guidewire in the presence of flow when the guidewire is introduced into a vessel, duct or lumen of a human being. This collapsible member functions as a sail-like construct for the distal portion of the guidewire, directing the guidewire in the area of maximal flow. The collapsible member is held in the expanded position by the flow within the vessel, duct or lumen.

In accordance with one preferred embodiment of this invention, the collapsible member mounted may be mounted at or near the distal tip of the guidewire or catheter. The collapsible member may be used to direct the guidewire through a narrowing or stenosis within a vessel, duct or lumen. In the situation where the diameter or cross-sectional area of the narrowing or stenosis is smaller than the diameter or cross-sectional area of the collapsible member when it is in the expanded position, the collapsible member may collapse, deform, fold or otherwise decrease its diameter to allow it to advance through the narrowing or stenosis. As described above, orientating a guidewire into the lumen of a narrowing or stenosis of a vessel, duct, or lumen is often one of the most challenging aspects of percutaneously treating diseases of blood vessels and other tubular structures. The technology described would utilize the increased flow velocity within a stenosis or narrowing and associated directed flow vectors to guide the tip of a guidewire or catheter with a sail mounted at or near the distal end into the lumen of a narrowing or stenosis even if that narrowing or stenosis was eccentrically placed within the lumen or did not have a smooth transition from the proximal portion of the vessel.

In accordance with another aspect of this invention, there may be one or more collapsible members mounted to a guidewire or catheter. The collapsible members in a collapsed position or expanded position may have a similar diameter or cross-sectional area as that of the guidewire or catheter or may have a diameter or cross-sectional area that is several times larger than the guidewire or catheter.

In accordance with another aspect of this invention, the device consisting of a collapsible member mounted on a catheter or guidewire may have one or more areas of the catheter or guidewire which may be able to be directed (i.e. steerable) by forces other than flow. In one embodiment, there may be a sail construct at or near the distal end of the guidewire and proximal to the sail the guidewire may be able to be flexed or bent in one or more directions by manipulating controls at or near the proximal end of the wire, possibly from outside the body of the patient. In this manner, the wire or catheter could be directed into the general direction of a particular vessel, duct or lumen or a branch thereof and the sail construct could guide the wire or catheter into a desired vessel, duct or lumen. For example, if the device was being advanced through the aorta and one wanted to selectively advance the device into the left common carotid artery, the device could be flexed so the distal end which included the sail construct was positioned near the takeoff of the left common carotid artery. The sail construct would then be affected by the flow entering the left common carotid artery and it would direct the catheter into that vessel selectively.

In accordance with another aspect of this invention, the device could be constructed to be used in very small vessels such as cerebral anatomy or in pediatric patients where the device would be constructed in dimensions smaller than currently used guidewires or catheters to advance the treatment diseases.

In accordance with another aspect of this invention, the sail construct which may be attached or integrated into a guidewire or catheter may be non-collapsible.

In accordance with another aspect of this invention, the sail construct may be collapsed or expanded by forces other than flow within the lumen of the vessel, duct, or lumen or contact with the wall or other material within the vessel, duct or lumen. The sail may be collapsible by a number of different methods including but not limited to vacuum evacuation of volume within a multilayer sail construct, increasing the distance between proximal and distal attachment points of a sail construct or advancing another construct (i.e. tube) over the sail construct and contact with the wall of a vessel duct or lumen or a narrowing within a vessel duct or lumen.

BRIEF DESCRIPTION OF THE DRAWINGS

Other aspects and many of the attendant advantages of this invention will readily be appreciated as the same becomes better understood by reference to the following detailed description when considered in connection with the accompanying drawings wherein.

DETAILED DESCRIPTION OF THE INVENTION AND PREFERRED EMBODIMENTS

Before the constructs are described, it is to be understood that this invention is not intended to be limited to the particular constructs and methods described in the preferred embodiments, as one skilled in the art can extend the concepts involved using variations which are obvious after reading the present disclosure.

It must be noted that, as used in this specification and the appended claims, the singular forms "a", "an", and "the" include plural referents, unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred compositions, films, methods and materials are described below.

Figure 1:
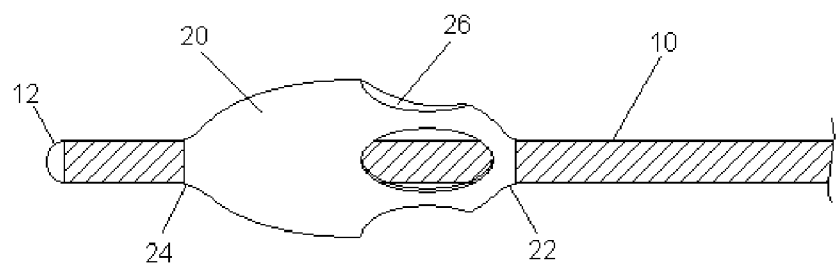
FIG. 1 is an enlarged isometric view of a portion of a guidewire with a sail mounted near its tip.

A preferred embodiment is shown in FIG. 1 where a guidewire 10 with distal tip 12 is constructed in standard fashion and mounted on the guidewire is a sail 20. A sail is defined as any projection or expansion which extends from a wire, catheter or other object which can impart a drag force to the object in the presence of flow around or in the region of an object. This technology overcomes previous technologies that one or more of the embodiments herein impart more drag to the object when flow is in one direction with relation to the object than in the opposite direction. In the embodiment shown in FIG. 1, when the device is in a vessel, duct, or lumen in the presence of flow of a fluid (air, liquid, semi-solids, solids or any combination thereof) the sail will impart more drag to the guidewire when flow is from the proximal to distal end of the device rather than the distal to proximal end, in FIG. 1 to the right is the proximal end and to the left is the distal end. When flow is from distal to proximal past the device in FIG. 1 and in one or more other embodiments in this description, the drag may be less than the other direction and the sail may partially or completely collapse against the guidewire, catheter or other object. This concept may be referred to as differential drag. With the drag forces imparted to the guidewire or catheter by flow in one direction may be more or less than the drag forces imparted to the guidewire or catheter by flow in the opposite or a different direction. The sail in FIG. 1 may be collapsed against the guidewire unless the device is in the presence of flow from the proximal to distal direction where the flow holds open the sail to impart drag to the guidewire. The sail may collapse while it is in the presence of proximal to distal flow if it encounters an outside force, such as the wall of the vessel or a stenosis. The sail may be made of a thin, flexible material such as a plastic. A non-exclusive list of materials for the sail (or other portions of the catheter) is included in Table 1. The sail may be very flexible such that it collapses under the force of gravity or it may be more rigid and retain an open position until it has contact with another object. The sail is designed to be collapsible when it is advanced through a stenotic vessel. As the sail directs the end of the guidewire into the stenosis and the sail contacts the walls or edges of the stenosis the sail may collapse against the guidewire and the crossing profile of the device may be just that of the guidewire or only slightly larger than the guidewire. The thickness of the wall of the sail may be very thin—about 0.0001 inches (about 2.5 microns) or less, or may be thicker depending on the application. For applications such as crossing coronary lesions, the sail may be very thin and flexible so that in the presence of flow it is in the expanded position and directs the guidewire to the area of maximal flow but once the guidewire is within the stenosis, the sail collapses against the guidewire with minimal force and minimal trauma to the stenosis wall or edge so the guidewire may be easily advanced through the stenosis.

Standard coronary guidewires have floppy tips. These floppy or very flexible tips and the very flexible "flow directed" catheters in the prior art are designed to be deflected in the presence of flow within a vessel such as the tip will tend to stay within the streamlines of flow within a vessel. These tips may be directed by forces which cause deflection of the tip perpendicular to the axis of the guidewire or catheter. In the presence of a stenosis, the flow may be turbulent or near turbulent at or near the opening of the stenosis and given that the flow in this transition region from the vessel to the lumen of a stenosis may not be perfectly streamlined and thus the tip of the guidewire or catheter may be subjected to multiple forces such that the reliance on tip deflection as a means to guide the tip into the lumen of the stenosis may not be sufficient, as is shown to be the case clinically. If all stenosis were characterized by a smooth taper into a lumen (concentric or eccentric) a flexible tip may more consistently be directed into the lumen of a stenosis by deflection of the tip of the guidewire. However, due to the fluid dynamic phenomenon associated with irregularly shaped stenoses and pusatile flow this does not always occur. The advancement described herein in part utilizes the streamline flow and increasing flow velocity which occurs in the presence of a stenosis to direct the tip of the guidewire. This technology may utilize a floppy or flexible tip which responds to forces and results in deflection of the tip perpendicular or nearly perpendicular to its axis, but importantly it also, by the presence of the sail, harnesses the energy of the flow parallel to the axis of the guidewire and drag forces are imparted to the guidewire (or catheter) via the sail in the vector which is along or in the general direction of the axis of the guidewire. In this manner the sail in effect works to pull the guidewire into the lumen of the stenosis.

The distal tip of the guidewire or catheter of this device may be very flexible or floppy such that under the force of gravity the distal tip is bent relative to the proximal portion of the guidewire up to the extent that it deflects 90 degrees in the direction of gravitational force. This may result in optimal guidance of the guidewire through a stenosis. The sail may be mounted anywhere along or proximal to this very flexible portion. The guidewire may also need to retain a degree of pushability at or near its distal end. When the flexible tip of the guidewire with a sail on it is pulled into a stenosis by drag forces there will be a degree of friction between the guidewire, sail and walls of the stenosis and depending on the length, the relative diameter of the stenosis to that of the guidewire and collapsed sail and the tortuosity of the stenosis the guidewire may need to retain a degree of pushability to advance the distal tip and sail through the stenosis. The situation should be avoided where the sail and distal tip are within a stenosis and there is insufficient pushability of the guidewire along one or more of its aspects resulting in difficulty in advancing the tip of the guidewire and sail through the stenosis. This may result in kinking or bunching of a portion of the guidewire within a stenosis and the inability to completely cross the stenosis. However, in some situations the very flexibility distal tip may be the best approach all of these aspects of this invention discussed herein may be modified and may be included in any combination to optimally achieve clinical success depending on the situation.

Many sail designs can be considered which could direct the tip of a guidewire or catheter into a lesion. The preferred embodiment shown in FIG. 1 includes a sail 20 with proximal end 22 and distal end 24 with one or more openings 26 in the proximal portion of the sail 20. These openings 26 allow the sail 20 to be attached to the guidewire at the proximal 22 and distal ends 24 of the sail, allowing the sail a tapered design to facilitate collapse of the sail and smooth transition of the device whether it is advanced or withdrawn through a lesion, stent, guide catheter or other device. The openings 26 allow flow into the sail wherein the sail may impart drag to the guidewire. The taper of the proximal and distal ends of the sail may be different and there may be a cylindrical portion to the sail at its maximal diameter.

TABLE 1

Examples of Polymers for Construction of the Sail

Silicon
Nylon
Polyethylene terephthalate
Latex
Nitrile
Epichlorohydrin
Viton
Ethylene-propylene
Butyl
Neoprene
Nitrile polyvinyl chloride
Silicone
Polyurethane
Hypalon
Phosphonitrillic-Halide
PTFE
Thermoplastic olefin blends
Polyvinyl chloride
Polythermide
Polyphenylsulfone
Polypropylene
Polyetheretherketone
Fluoroelastomers
Polyethylenes
Polyesters
Polyimide The sail 20 may be constructed of a material which is elastic in nature. A portion or the complete sail may be somewhat elastic. This may facilitate the collapse of the sail against the guidewire when the guidewire is not n the presence of flow and when it is being advanced through a lesion. As an example, the distal aspect of the sail may be elastic or have a secondary elastic component (band, wrap, cover, etc.) which promotes collapse of the sail on the guidewire while the proximal portion is not elastic and easily opens in the presence of flow. The elasticity of the sail may be such that in the presence of a certain amount of flow, the sail will open to impart drag to the guidewire and be closed when there is too little or no flow.

Figure 2:
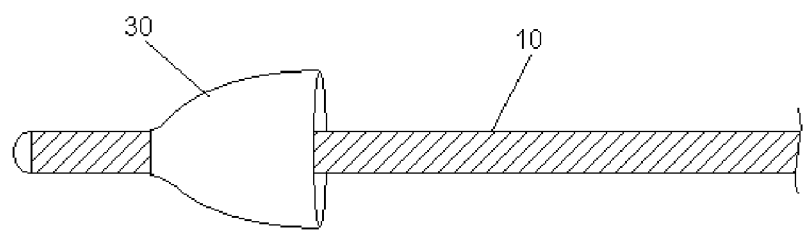
FIG. 2 is an enlarged isometric view of a portion of a guidewire with a sail with an open proximal portion mounted near its tip.

Shown in FIG. 2 is a preferred embodiment of the construct which includes a guidewire 10 and a sail 30 attached to the guidewire. The sail 30 has a distal end which is closed and a proximal end which is open. The sail 30 may have a shape similar to a half sphere, half cone or any other similar shape. In this embodiment, the sail 30 imparts drag to the guidewire and may collapse around the guidewire in the presence of contact in accordance with the flexible and deformable nature of the sail. The portion of the guidewire in the region of the sail may be of smaller diameter than some or the entire remaining portion of the guidewire. This may allow the crossing profile of the construct to be uniform with the sail fully collapsed against the guidewire. In the presence of flow, the sail 30 would be in the expanded position, as is shown in FIG. 2. As the construct was being withdrawn through a lesion or through the area where a lesion had been treated with a stent, angioplasty, or other therapy, the sail 30 may be sufficiently flexible as to evert or fold over on itself and assume the same shape in the reversed direction to facilitate easy removal of the construct from an vessel, duct, or lumen. Additionally, another catheter such as a simple tube or tapered tube with an inner diameter slightly larger than the outer diameter of the guidewire or the guidewire plus the collapsed sail could be advanced over the guidewire up to and possibly over the sail to facilitate easy removal of the construct from a vessel. As this catheter is advanced over the sail 30 the sail may evert and collapse against the guidewire to facilitate retraction of the device through vessel or other catheter. Additionally, the sail may evert in the presence of flow. In an everted position, the sail would still impart drag to the guidewire and may direct the guidewire into the lumen of a stenosis or narrowing.

Figure 3:
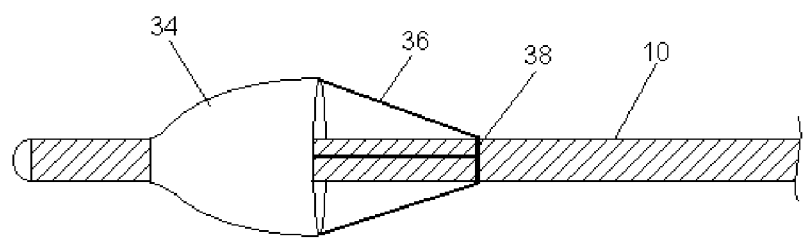
FIG. 3 is an enlarged isometric view of a portion of a guidewire with a sail with proximal attachments to the guidewire.

Shown in FIG. 3 is a preferred embodiment of the construct which includes a guidewire 10 and a sail 34 attached to the guidewire. The sail 34 may be attached to the guidewire at its distal aspect and may also be attached to the guidewire by one or more retention attachments 36 which attach to the guidewire 10 at or more proximal than the proximal end of the sail. The retention attachments 36 may be secured to the guidewire 10 by band 38 or other configuration which itself is attached to the guidewire 10. These retention attachments 36 may prevent the undesired eversion or turning inside out of the sail 34 in the presence of normal flow, during removal through a treated or untreated vessel, or when another catheter is being advanced over the balloon. To facilitate removal of the guidewire with the sail in place, a tube or other catheter could be advanced to the sail, and it would be guided over the sail by the retention attachments to collapse the sail against the guidewire.

Figure 4:
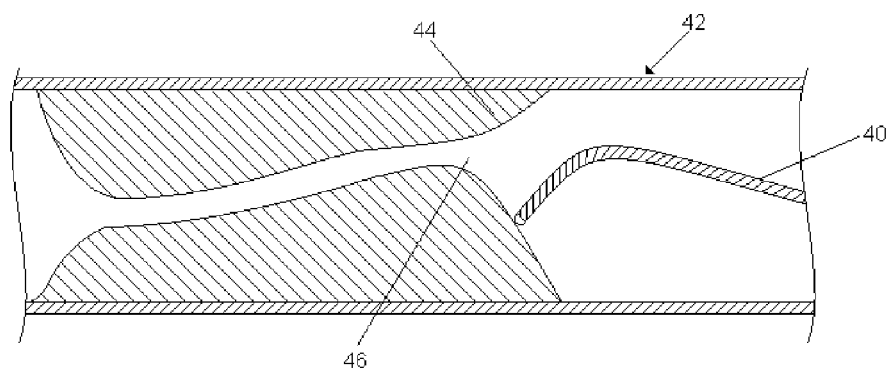
FIG. 4 is an enlarged longitudinal sectional view of a portion of a traditional guidewire within a vessel with a stenosis.

Although traditional guidewires have floppy distal ends, they are not sufficiently directed by the flow of the blood through a lesion to reliably be guided into the ostium of the lesion or stenosis. Shown in FIG. 4 is a guidewire 40 within a vessel 42 with a stenosis 44 with an eccentric opening 46. The vessel has flow of blood from the proximal to distal direction, from right to left in the Figure. The guidewire 40 may be difficult to advance through the opening 46 of the stenosis 44 and may become lodged in the proximal aspect of the stenosis and only further flex in response to further advancement by the operator as is shown in FIG. 4.

Figure 5:
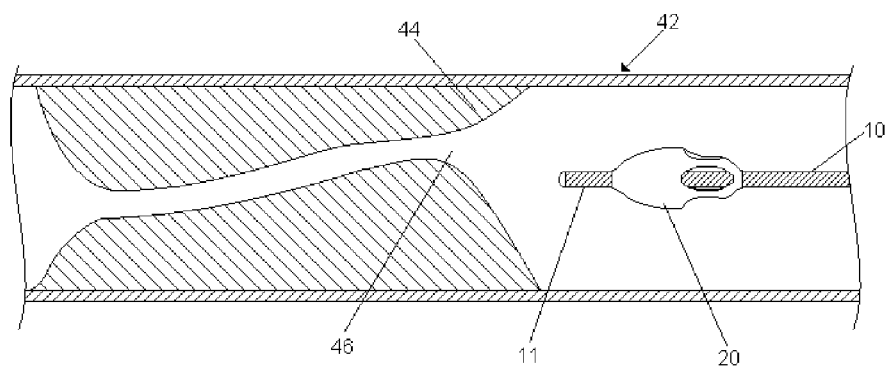
FIG. 5 is an enlarged longitudinal sectional view of a portion of a guidewire with a sail mounted near its tip within a vessel with a stenosis.
Figure 6:
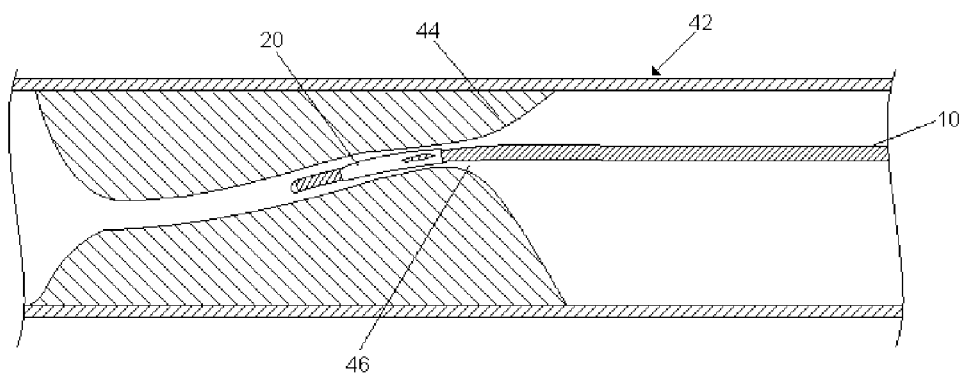
FIG. 6 is an enlarged longitudinal sectional view of a portion of a guidewire with a sail mounted near its tip advancing through a stenosis within a vessel.

Shown in FIG. 5 is a guidewire 10 with a sail 20 attached near the distal tip of the guidewire. The guidewire 10 is within a vessel 42 with a stenosis 44 with an eccentric opening 46. The sail 20 is in the expanded position with flow within the vessel and through the lesion maintaining the sail in the expanded position and imparting drag force to the guidewire. As the distal aspect of the guidewire 11 and sail 20 approach the opening 46 of the stenosis 44, the blood flow in the vessel will begin to direct the guidewire into the stenosis. The velocity of the flow will increase and the direction of the flow will be into the opening of the stenosis as the cross-sectional diameter becomes smaller in the area of the stenosis. This flow will impart force to the sail and guidewire and direct the sail and guidewire into the opening 46 of the lesion 44. FIG. 6 shows the guidewire 10 and sail 20 with the sail now in a collapsed position as it is within the lumen of the stenosis 44 within the vessel 42. The guidewire may now be easily advanced by the operator through the lesion and further treatment of the lesion with other technology such as angioplasty, stenting, atherectomy or other treatments known or which may be developed.

Figure 7:
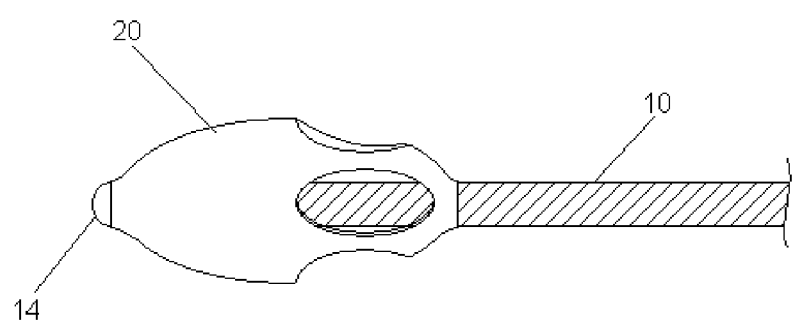
FIG. 7 is an enlarged isometric view of a portion of a guidewire with a sail mounted at its tip.
Figure 8:
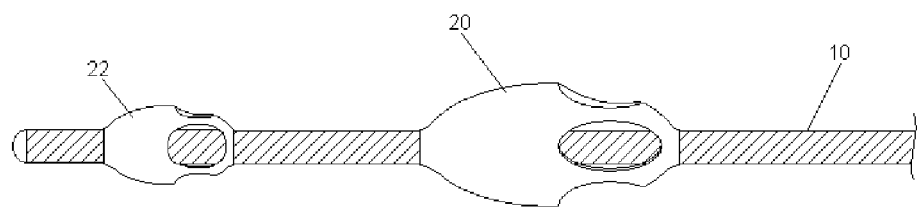
FIG. 8 is an enlarged isometric view of a portion of a guidewire with a sail mounted at its tip and a second sail mounted more proximally.

In another preferred embodiment, the sail may be mounted at the end of the guidewire. FIG. 7 shows a sail 20 mounted at the distal end of the guidewire 10. The sail 20 may have a distal tip 14 which is atraumatic. Additionally, there may be more than one sails mounted to a guidewire. FIG. 8 shows a proximal sail 20 and a distal sail 22 mounted to a guidewire 10. The sails may be of similar size or they may be of different sizes as shown in FIG. 8. The second sail may provide additional force, in the form of drag, to the guidewire so the guidewire is easily advanced through a stenosis. The proximal sail(s) may continue to direct the wire through the lesion and reduce any tendency of the wire to bend or kink at the ostium of the stenosis and make further advancement of the guidewire difficult.

Figure 9:
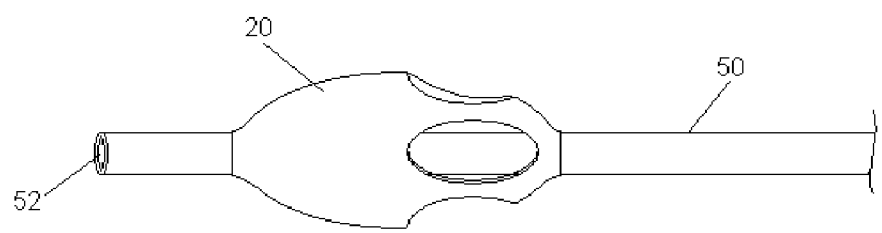
FIG. 9 is an enlarged isometric view of a portion of a hollow catheter with a sail mounted near its tip.
Figure 10:
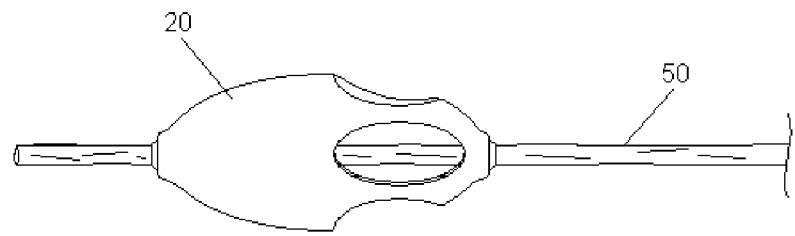
FIG. 10 is an enlarged isometric view of the hollow catheter of FIG. 9 with a sail mounted near its tip where the catheter is in a collapsed position.
Figure 11:
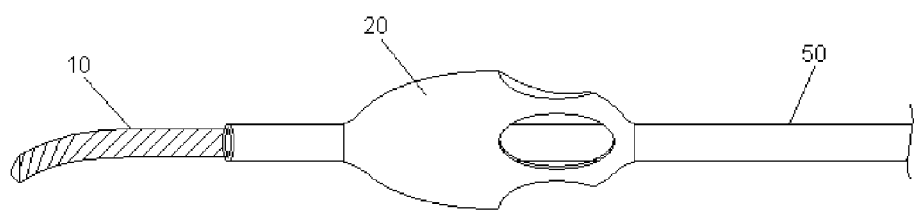
FIG. 11 is an enlarged isometric view of a hollow catheter of FIG. 9 with a sail mounted near its tip with a guidewire extending through the lumen of the catheter.

There may be other constructs which may be able to utilize the sail technology to advance a guidewire or catheter across a lesion. A construct may be utilized which has a catheter which is much more flexible (or perhaps less) than a guidewire. An ultra flexible catheter with a mounted sail may even be more directed by flow into the opening of a stenosis. Initial testing demonstrated that the more flexible the guidewire is, the more effected it is by the flow and directed into and across the stenosis. In a preferred embodiment, FIG. 9 shows a catheter 50 with a sail 20 mounted to it near its distal end. At the distal end of the catheter 50 there is an opening 52 which allows for the passage of a guidewire or another catheter. The catheter 50 may be very flexible and may be constructed of an elastic material which allow the body of the catheter to collapse into a smaller diameter when there is no guidewire or catheter within its lumen as is shown in FIG. 10. The catheter may be more elastic in one portion of the catheter than another portion. For example the catheter may be more elastic in the distal portion so it collapses to achieve a very small diameter and is less elastic in the proximal portion where it maintains a tubular shape and pushability. FIG. 10, the sail 20 is mounted to the catheter 50 and remains securely mounted if the catheter collapses. The sail itself may also collapse in the absence of flow. The catheter 50 may be advanced into a vessel via a guide catheter, over a guidewire or by itself or a combination thereof. Once the catheter is proximal to a lesion, in the presence of flow the sail may expand and provide drag force to the catheter. The catheter may remain in the collapsed position. The catheter may be constructed of a very thin wall rendering it very flexible. The catheter may have a thinner wall in one portion than another. For example the distal portion of the catheter may have a thinner wall and be more flexible while the proximal portion has a thicker wall and thus the catheter has excellent pushability and transmission of torque. The catheter may be constructed of a material which can undergo a degree of plastic deformation and thus a portion of the catheter, such as the distal tip may be bent to allow the catheter to be steered into a selected vessel, duct, or lumen. With the catheter 50 in a collapsed position, the crossing diameter of the catheter may be very small, much smaller than the typical 0.014 inch (360 microns) crossing profile of a guidewire. This small and flexible catheter may allow it to cross very tight lesions which would be more difficult to cross with a guidewire. The flow within the vessel may direct the catheter and sail through a stenosis, aided by the advancement of the catheter by the operator. Shown in FIG. 11, once the catheter 50 and sail 20 are across the lesion, a guidewire 10 may be advanced through the catheter. The guidewire 10 may be a traditional guidewire as is shown or may be a guidewire with a distal protection device such as a balloon or filter attached. Another catheter such as that which may provide radiation, thrombectomy or be used to open or cross a total occlusion could be advanced through the catheter 50. If a guidewire 10 or other device is advanced through the catheter 50, the catheter 50 may be withdrawn from the vessel and then the stenosis may be treated by any available means (i.e. stenting). Another application of these embodiments may be to utilize the tubular construct with a mounted sail to deliver therapeutic or biologically active agents (i.e., drug, gas or other biologically active agent, compound, molecule or other matter) in the form of a fluid, solid or any combination there of. The delivery of said agents may beneficially effect a living being.

In some applications it may be useful for a guidewire with a sail mounted at or near the end to be directable, or steerable to guide the sail into the path of desired flow so it may access a target vessel. With other outside control, the sail will direct the guidewire or catheter it is mounted on or integrated within into the vessel, duct, or lumen with the greatest flow. At times, there may be one or more vessels with significant flow so as the catheter or guidewire approaches two vessels at a branch point, the catheter or guidewire may not always be directed into the desired vessel. If the sail is mounted proximal to the tip of the guidewire, the tip of the guidewire may be shaped or angled in standard fashion as to make the guidewire steerable by directing the tip of the guidewire into the lumen of the desired vessel by torquing the guidewire. There are other applications where this simple manipulation is not adequate. Carotid stenting is emerging as an important means for treating carotid atherosclerotic disease. The most difficult part of carotid stenting is establishing access to the common carotid artery with a guide catheter as is currently done. Atherosclerosis is a systemic disease. Patients with clinically significant carotid atherosclerotic disease often have diseased aortas and undergo significant risk of an embolic event when a guide catheter is advanced from the groin into the innominate or left common carotid branch off the aorta. Seating the guide catheter in the innominate or left common carotid branch often requires significant manipulation of the guide catheter within an atherosclerotic aorta. Depending on the tortuosity of the innominate or left common carotid branch, seating this guide catheter can be difficult, time consuming and expensive as often multiple different guiding catheters are used. The combination of a steerable guidewire and a sail for guidewire direction can overcome the difficulties of accessing the common carotid artery from the aorta and minimize the risk of embolization of plaque from the aorta into a carotid artery by minimizing contact with wall of the aorta. Rather than focusing on steering a guidewire at the tip, a preferred embodiment of this invention positions a sail near the distal tip of a guidewire or catheter and a steerable portion proximal to the sail. This allows the sail to be directed into the area of the desired vessel, for example the left common carotid branch off the aorta, then utilizes the flow into that branch to direct the sail and guidewire into that branch. Additionally, the guidewire also has a traditional floppy tip which can be angled in usual fashion to provide an additional means of directing or steering the guidewire. Alternatively there may be one or more sails proximal to the steerable portion of the guidewire in addition to or instead of the sail(s) distal to the steerable portion of the guidewire.

Figure 12:
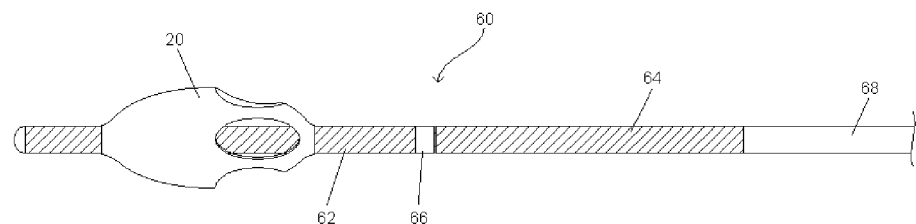
FIG. 12 is an enlarged isometric view of a portion of a steerable guidewire with a sail mounted near its tip.
Figure 13:
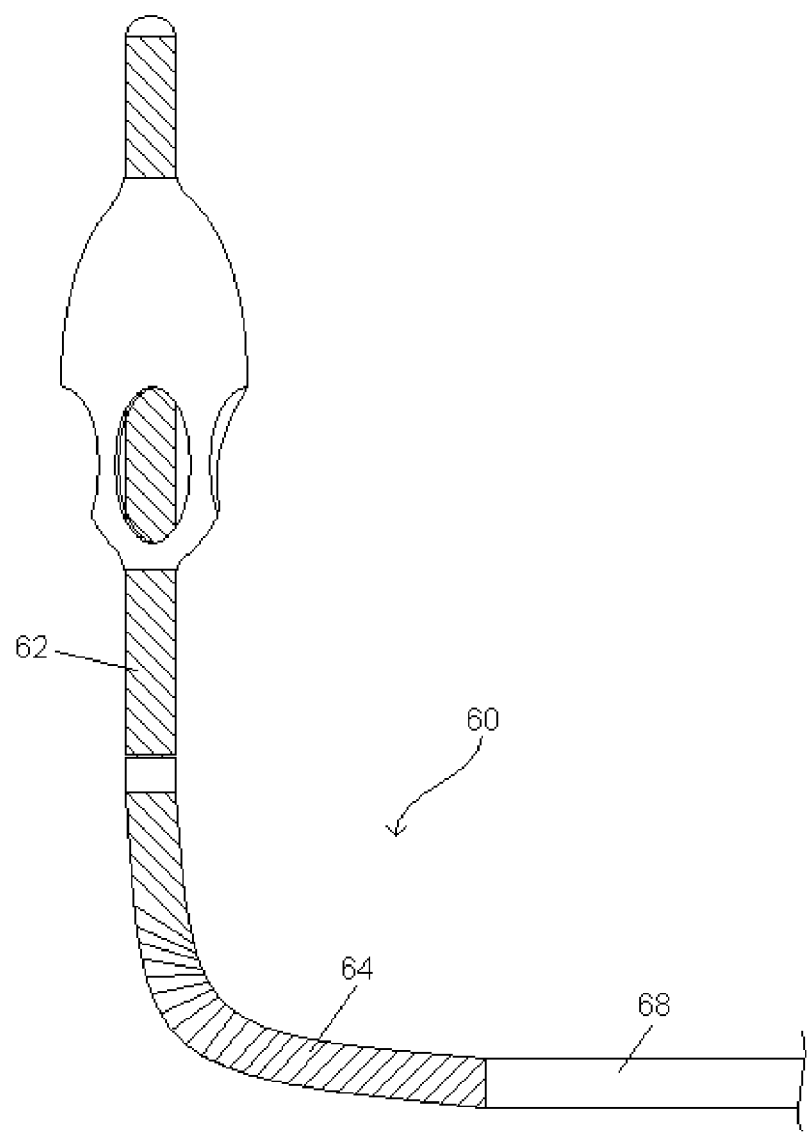
FIG. 13 is an enlarged isometric view of the steerable guidewire with a sail mounted near its tip shown in FIG. 12 with the tip of the catheter at an angle with respect to the proximal portion of the catheter.
Figure 14:
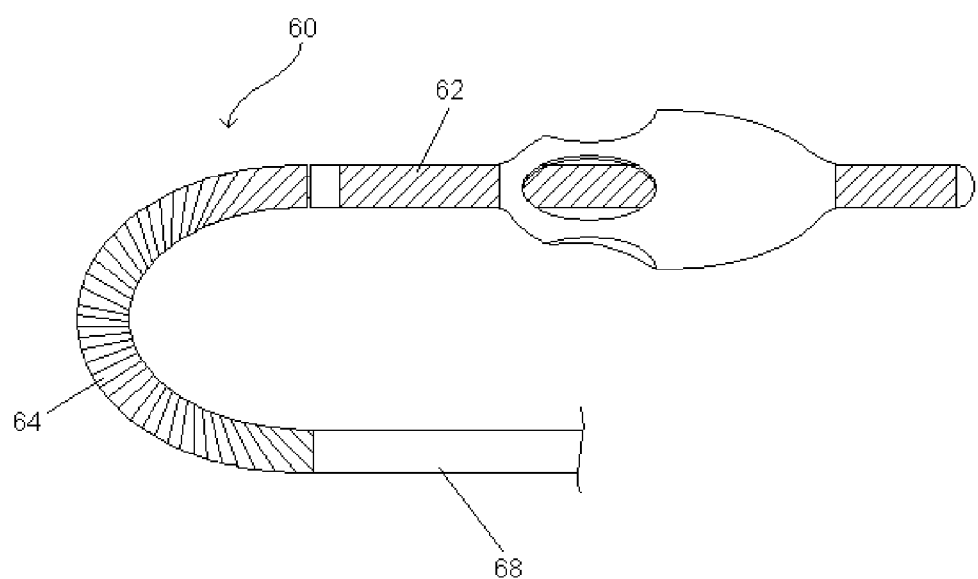
FIG. 14 is an enlarged isometric view of the steerable guidewire with a sail mounted near its tip shown in FIG. 12 with the tip of the catheter at an angle with respect to the proximal portion of the catheter.

FIG. 12 shows a guidewire 60 with a sail 20 mounted on a distal portion of the guidewire 62 adjacent to a steerable portion 64. The steerable portion 64 is located proximal to the sail 20. The steerable portion 64 is joined to the distal portion 62 at a linking member 66 at its proximal end. There may additionally be a proximal portion of the guidewire 68. The steerable portion 64 may be flexed or bent at the direction of the operator to angle the distal portion of the guidewire within a vessel. FIG. 13 shows the guidewire 60 with its distal portion 62 bent at an angle with respect to the proximal portion 68 as the steerable portion 64 forms a gentle curve. FIG. 14 is another view of the guidewire 60 with the distal portion 62 approximately parallel to the proximal portion 68 by nature of a marked curve formed by the steerable portion 64. The steerable portion 64 may be able to bend up to or further than a 180 degree angle. This feature is important for allowing the sail to be directed within the aorta towards a desired head or arm vessel.

Figure 15:
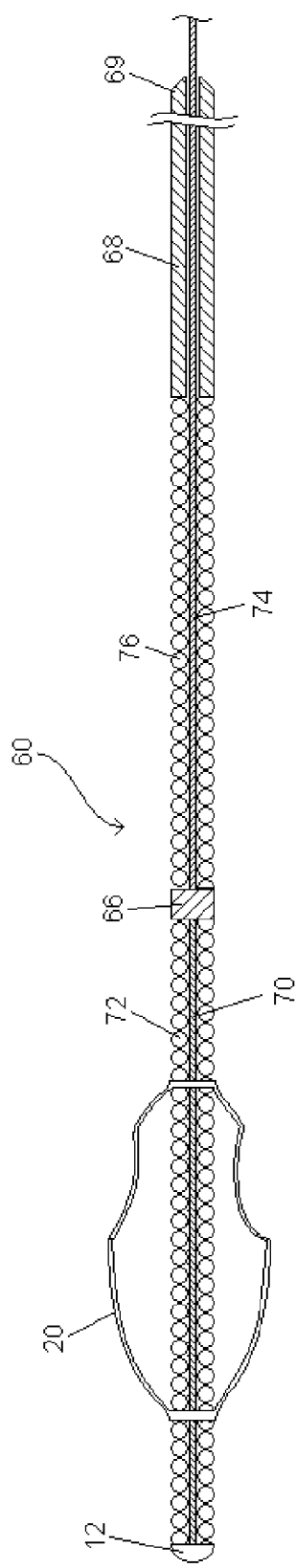
FIG. 15 is an enlarged longitudinal sectional view of the steerable guidewire with a sail mounted near the tip as shown in FIG. 12.

A preferred embodiment of the mechanics for the steerable guidewire with sail direction are shown in the FIG. 15. This cross-sectional view of the guidewire 60 shows a distal portion which is constructed in standard fashion with a distal core wire 70 and a wire coil 72 wrapped around the core wire. The distal core wire 70 is attached proximally to the linking member 66 and distally to the tip 12. The sail 20 is attached to the distal portion of the guidewire. The center wire or steering wire 74 of the steerable portion attaches to the linking member 66 of the proximal portion of the guidewire. A coil of wire 76 is wrapped around the steering wire 74. This steering coil may be attached proximally to a proximal tube portion 68 of the guidewire, and it may be attached distally to the linking member 66. The steering wire 74 may be attached in the center of the linking member 66 or it may be attached closer or at the edge of the linking member. An eccentric position of this joint may improve the ease of steering of the device. The proximal tube 68 of the guidewire has a proximal end 69 and the steering wire 74 extends proximally beyond the proximal end 69 of the proximal tube 68. The proximal end 69 of the proximal tube 68 may have a feature such as a chamfered end which allows it to easily be passed into a steering device. The steering mechanism of the guidewire is utilized by retracting the steering wire 74 proximally relative to the proximal tube 68. When this is done, the steering coil 76 is flexed as the distance between the linking member 66 and the distal portion of the proximal tube 68 decreases. This allows the bending of the steerable portion shown in FIGS. 13 and 14. The eccentric positioning of the joint between the steering wire 74 and the linking member 66 may determine the direction which the distal portion of the guidewire will bend relative to the proximal portion. This known direction of bending may be marked at or near the proximal end of the guidewire so the operator knows how to position the wire so it will be steered in the desired direction.

Figure 16:
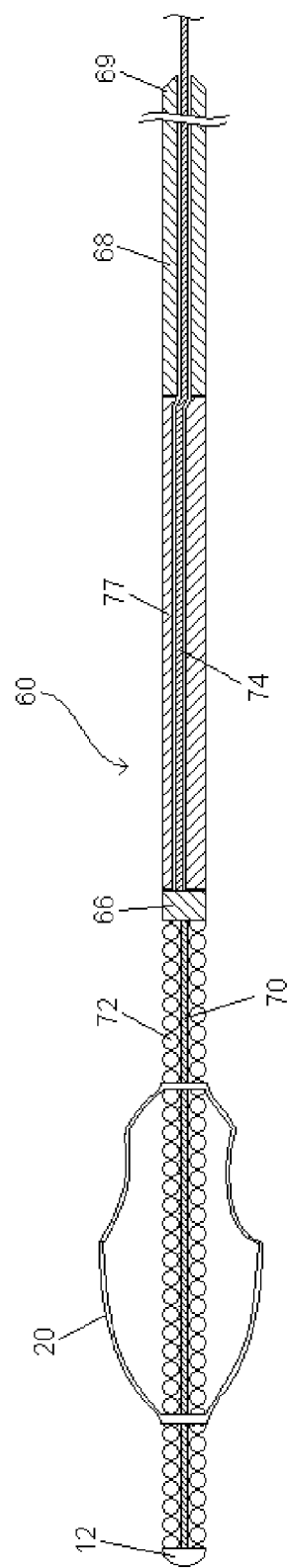
FIG. 16 is an enlarged longitudinal sectional view of another embodiment of the steerable guidewire with a sail mounted near the tip as shown in FIG. 12.

FIG. 16 shows another preferred embodiment of the steerable guidewire with sail technology. The guidewire 60 has a distal portion as described for FIG. 15 with a distal core wire 70, distal coil 72, sail 20, distal tip 12 and linking member 66. The steerable portion has a steering wire 74 and proximal tube 68 with proximal end 69. Instead of the coil around the steering wire, this embodiment has a flexible tube 77 which the steering wire 74 passes through. The flexible steering tube 77 may be attached to the proximal tube 68 and may be attached to the linking member 66. The steering tube 77 may be concentric or it may have a central lumen which is eccentrically located in the tube. Additionally, as described for the embodiment in FIG. 15, the steering wire may be attached to the linking member in a concentric or and eccentric fashion. The eccentric steering tube may direct the distal portion of the guidewire in a particular direction. This may improve the ease of use of the device and eliminate a trial and error initial steering move to determine which direction the device will bend within a vessel.

The components of the guidewire may be made of a number of materials. The core wire, steering wire, coils and proximal tube and linking member may be made of stainless steel, nitinol or another alloy or any non-metal. They need to have sufficient strength to resist breakage and adequate flexibility to achieve the degree of steering desired and be atraumatic to the tissues. Portions of the guidewire may be coated with Teflon or another lubricious coating to ease advancement of other catheters over the guidewire. The guidewire 60 shown in FIGS. 12 through 26 may have a diameter of 0.035 inches (890 microns). This would be a typically diameter for a guidewire used to gain access to a carotid vessel through a guiding catheter. Alternatively, the guidewire may have a smaller diameter even as small as 0.014 inches (360 microns) or smaller. This may allow the guidewire to be used for other applications in smaller vessels. The guidewire may of course have a diameter of larger than 0.035 inches (890 microns) for some applications.

Figure 17B:
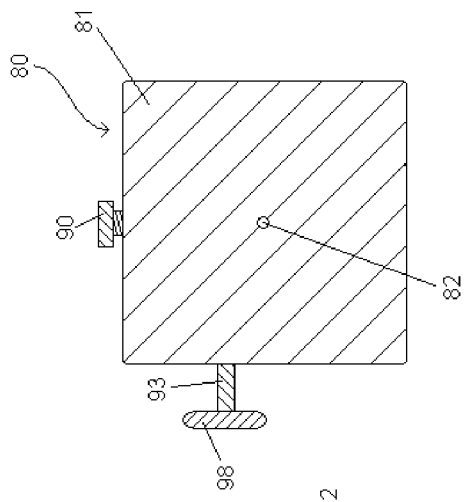
FIG. 17*b* is a side elevation view of the device shown in FIG. 17*a* which used to control the steerable features of the guidewire shown in FIG. 12.
Figure 17A:
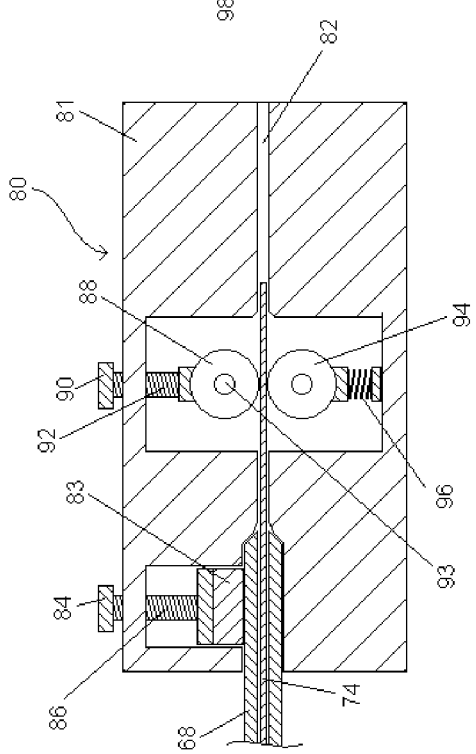
FIG. 17*a* is a longitudinal sectional view of a device used to control the steerable features of the guidewire shown in FIG. 12.

The steering of the guidewire may be accomplished by pulling on the steering wire relative to the proximal tube at the proximal end of the guidewire. Although this could be done with such simple instrumentation as a clamp, a device which allows the operator to easily make fine adjustments of the position of the steering wire relative to the proximal tube would be useful. Such a device is shown in FIGS. 17a and 17b. A side cross-sectional view is shown in FIG. 17a where the proximal tube of the guidewire 68 and the steering wire 74 enter the steering device 80. The device has a case 81 and several other features to hold the proximal tube 68 in place while adjusting the steering wire 74 proximally and distally relative the to the proximal tube. The steering device has a lumen 82 to accept the proximal tube 68 and steering wire 74. This lumen 82 decreases in diameter in a manner to match any end design on the proximal tube 68 to provide a mechanical stop for the proximal tube. The steering wire is then allowed to advance further into the steering device. The proximal tube 68 is locked in place relative to the steering device 80 by a locking pad 83 which is adjusted by a locking knob 84 which advances a screw threaded shaft 86 which runs through a threaded lumen in the device case 81. The force used to lock the proximal tube is sufficient to hold it but not so much that the lumen of the tube is narrowed and the steering wire 74 cannot be moved. There may be a clutch mechanism on the locking apparatus where the operator turns the locking knob 84 till it clicks and the clutch limits the torque which can be applied to the knob and thus limits the force which can be applied to the proximal tube. As the proximal end of the steering wire 74 is advanced into the steering device 80 it passes between a base roller 94 and an adjustment roller 88. The base roller 94 may be anchored to the case 81 via a spring 96 which maintains the desired level of tension between the base roller 94 and the steering wire 74. The adjustment roller 88 with shaft 93 may also be anchored to the case 81 via a spring or it may be adjustable in position relative to the steering wire by a screw threaded shaft and tightening knob 90. The tightening knob 90 may allow the adjustment roller to be loosened to allow easy advancement of the steering wire into the device and then tightened to provide adequate tension so the rollers can then advance and retract the steering wire. Spring mounted rollers may be able to accomplish this without an adjustable tensioning mechanism. Alternatively, the base roller may be mounted to the case without a spring and the adjustment roller may have a clutch mechanism as described for the locking pad 83. Once the base and adjustment rollers are tightened against the steering wire, the adjustment roller may be rotated to advance or retract the steering wire relative to the proximal wire to cause steering portion of the guidewire to bend. FIG. 17b is an end view of the steering device 80 with case 81. The lumen 82 may be open at the proximal end of the device as is shown. The steering wire may extend through the device out the proximal end of the lumen. This may give the operator assurance that the steering wire is moving relative to the steering device. In FIG. 17b, the tightening knob 90 is shown. The shaft 93 of the adjustment roller extends out of the device and an adjustment knob 98 is attached to it. The adjustment knob 98 is rotated by the operator to advance or retract the steering wire relative to the proximal tube to steer the guidewire. To bend the device from its straight position, the steering wire is retracted as discussed above. This is done by rotating the adjustment knob in a counter clockwise manner. To straighten the device fully or partially the adjustment knob is rotated in clockwise manner. The operator may choose to use the steering device with the adjustment knob directed vertically and the locking and tightening knobs directed horizontally. Not every mechanical detail of the steering device is shown; it is one embodiment of a simple device which could be used to steer the guidewire. Other embodiments could also be considered which used a thumb wheel similar to that found on a computer mouse, a handle which slides relative to the case or many other similar constructs could be considered.

Figure 18:
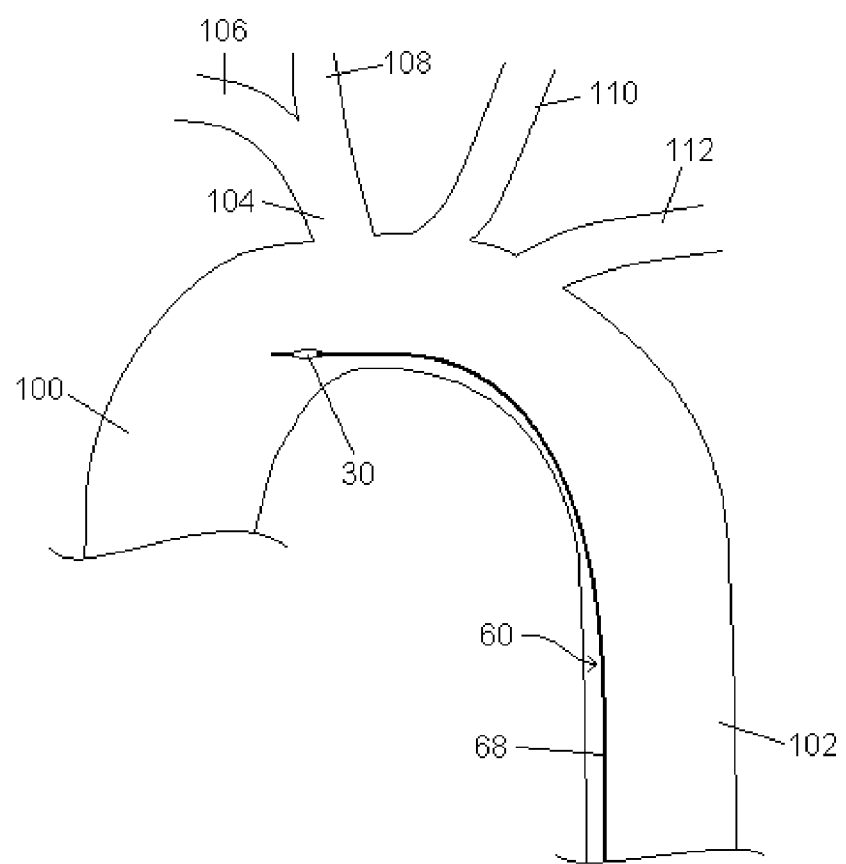
FIG. 18 is an enlarged view of a sail mounted on a guidewire within the aorta in partial section.
Figure 19:
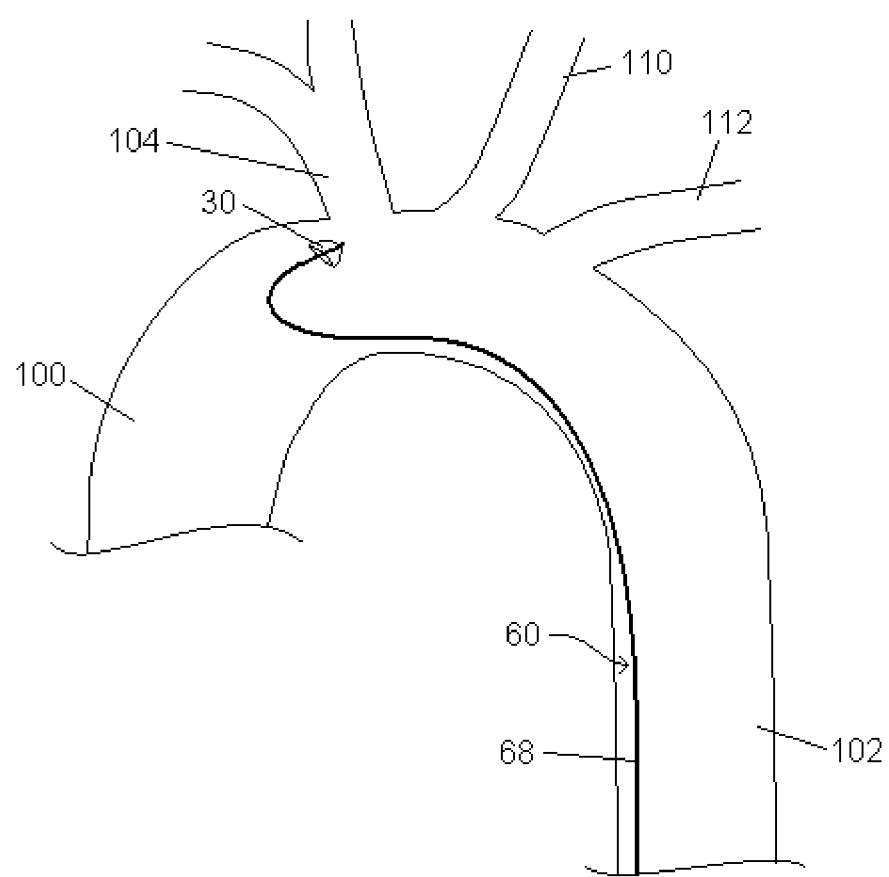
FIG. 19 is an enlarged view of a sail mounted on a guidewire of FIG. 18. with the guidewire angled proximal to its tip within the aorta in partial section.
Figure 20:
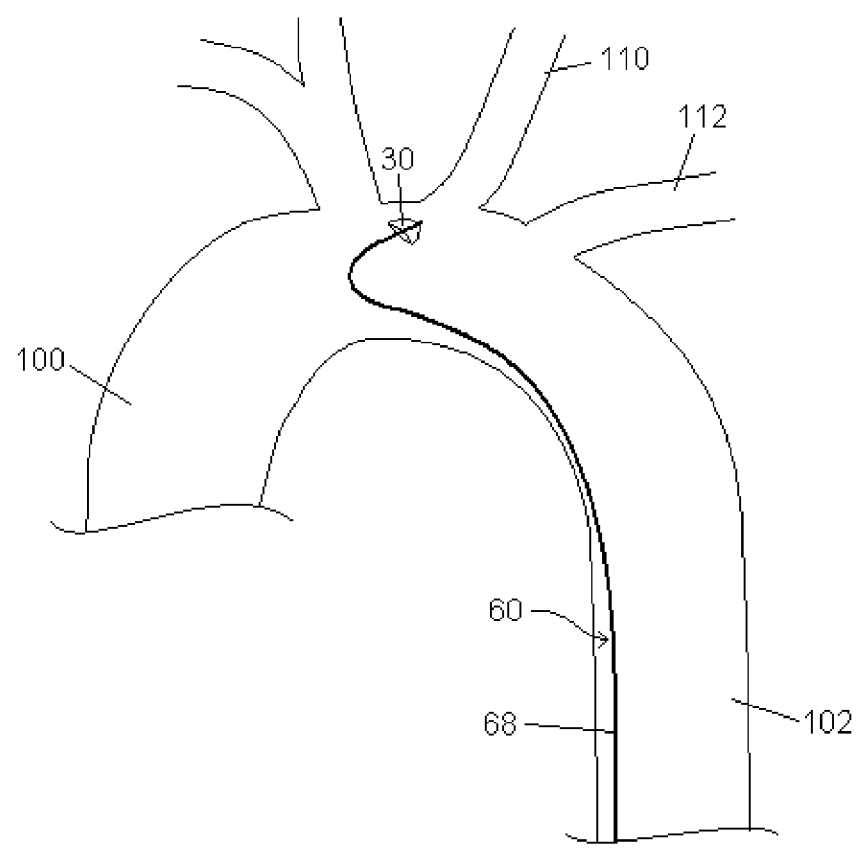
FIG. 20 is an enlarged view of a sail mounted on a guidewire of FIG. 18. with the guidewire angled proximal to its tip and retracted further within the aorta in partial section.
Figure 21:
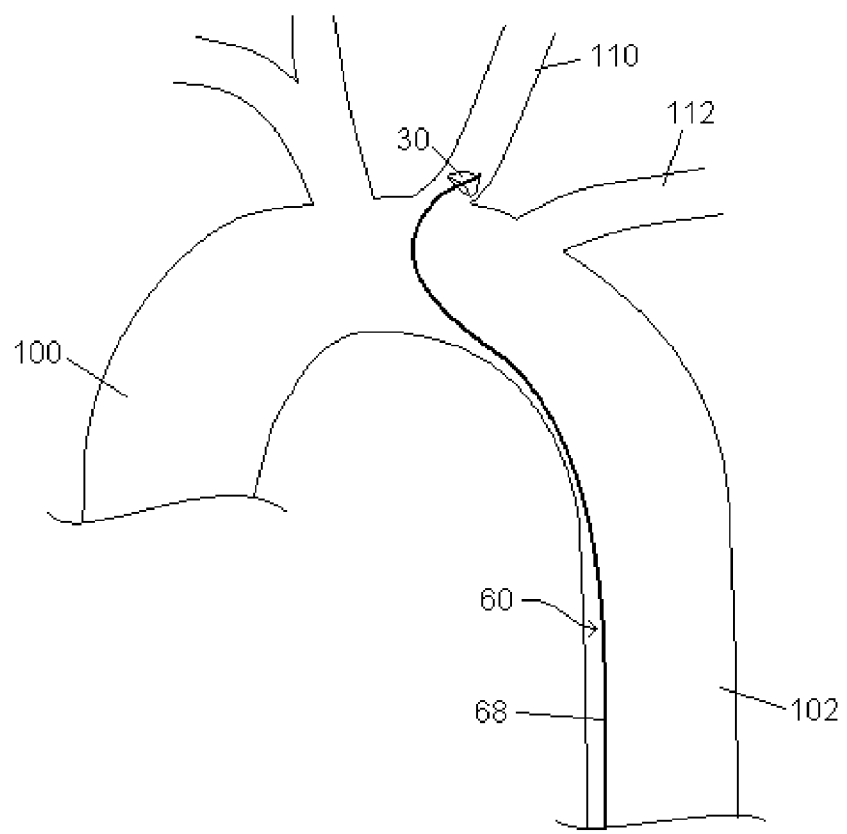
FIG. 21 is an enlarged view of a sail mounted on a guidewire of FIG. 18. with the guidewire angled proximal to its tip with the tip in the left common carotid branch of the aorta in partial section.

Illustration of the sail guidance of a guidewire or catheter with incorporated steering capabilities is shown in FIGS. 18 to 21. As described previously, a guidewire with an incorporated sail will be directed within a vessel according to the flow. If the guidewire and sail are in an area of the vessel with a branch, the sail may be directed into the branch if it is placed in the vessel in the direction of flow into the branch. In the application described previously, directing a guidewire or catheter into a selected branch off the aorta with minimal or no contact with the aortic wall and with minimal difficulty would be an improvement over current techniques. FIG. 18 shows a guidewire 60 with proximal portion 68 with sail 30 near the distal tip of the catheter. The guidewire 60 has been advanced retrograde through the descending aorta 102 until its tip is in the ascending aorta 100 or just distal to that in the aortic arch. The aorta usually has three branches off of it which supply blood to the head and neck. The innominate artery 104 which divides into the right subclavian artery 106, right common carotid artery 108, the left common carotid artery 110 and the left subclavian artery 112. To direct the tip of the guidewire 60 into a desired vessel, such as the left subclavian artery, the guidewire is advanced into the ascending aorta 100. In this position, the sail 30 is collapsed because its distal end is facing the direction of flow and it is only open at its proximal end. In order to have the sail direct the guidewire, the guidewire needs to be flexed or steered so the distal tip of the guidewire is pointing in the general direction of flow. FIG. 19 shows the guidewire 60 with the steerable portion as previously described flexed so distal tip and sail 30 are pointed in the direction of flow. The sail 30 has opened and is currently positioned in the arch of the aorta. It is near the orifice of the innominate artery 104 and may be directed by the flow into this branch vessel. If placement of the guidewire into the vessel is desired, the flex in the guidewire may be reduced, allowing the guidewire to straighten slightly and with gentle advancement, the guidewire may enter the innominate artery 104. For this example, the guidewire will be directed into the left common carotid artery 110. To do so, the guidewire is retracted in the flexed position as shown in FIG. 19. As it is pulled back through the aorta it will near the orifice of the left common carotid artery as is shown in FIG. 20. To advance the guidewire into the left common carotid artery 110, the guidewire is straightened slightly. With some advancement, the flow will direct the guidewire 68 into the orifice of the left common carotid artery 110. FIG. 21 shows the tip of the guidewire 60 with the sail 30 in the left common carotid artery 110. At this point, the guidewire, depending on its size and the pathology within the common carotid artery the guidewire could be advanced past a lesion in the common or internal carotid artery or it could be exchanged for a simple tubular catheter instead of a more expensive traditional guiding catheter. Additional guidewires, angioplasty balloons, distal protection devices, stents or other devices could be passed though this simple tubular catheter. With this easily controlled device, a guidewire may be positioned from the aorta into a desired branch vessel with minimal or no contact with the wall of the aorta and with improved ease compared to the currently available technology. This is simply one application for this technology. Accessing other vessels or selecting between branches of other vessels may also be desirable.

Figure 22:
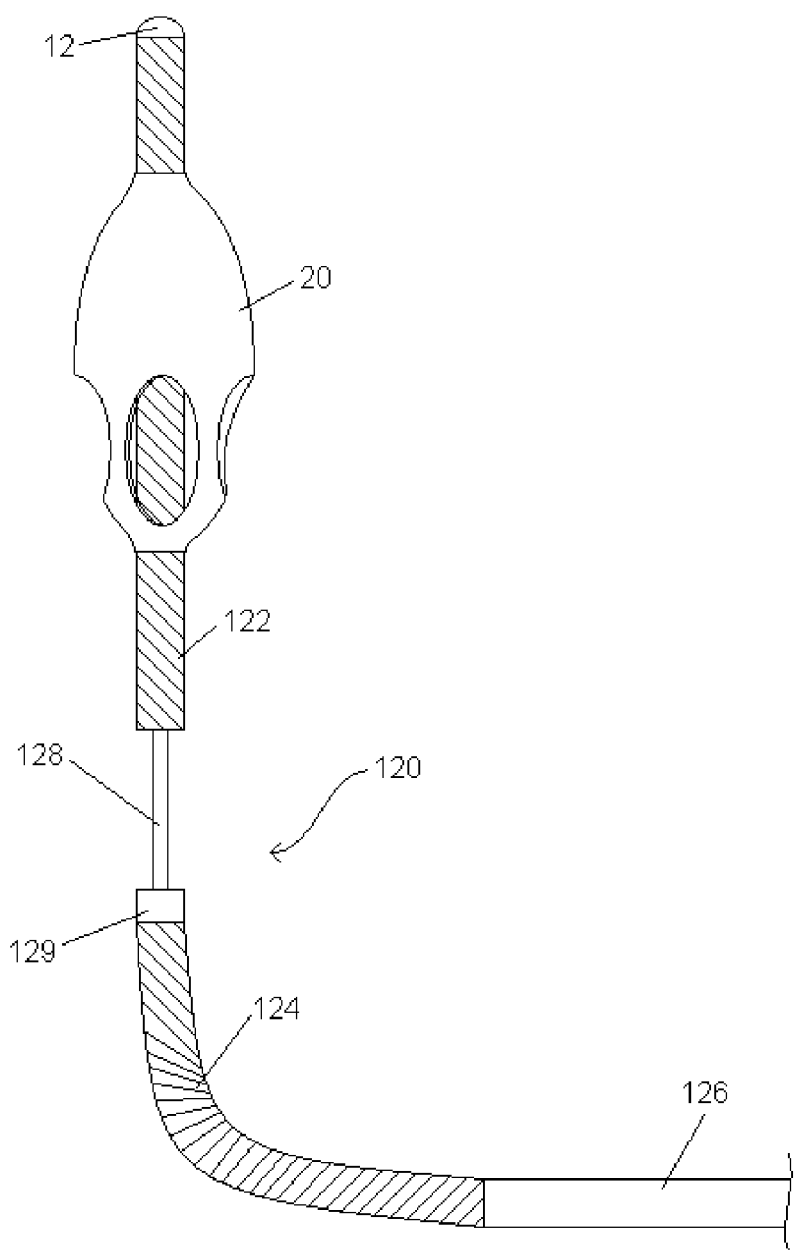
FIG. 22 is an enlarged isometric view of a portion of a steerable guidewire with a sail mounted near its tip and the distal portion of the guidewire extended distally.

Depending on the diameter of the aorta and the length of the distal portion 62 of the guidewire 60 as shown in FIG. 13, there may be a situation where the guidewire is flexed to position the sail in the orifice of a desired vessel such as the left common carotid artery and the sail is not optimally positioned to be directed by the flow into that artery. FIG. 22 shows another embodiment of a steerable guidewire 120 with sail 20 distal portion 122, steerable portion 124, linking member 129 and proximal portion 126. The guidewire 120 also has an extension apparatus 128 which permits the operator to increase the length between the distal tip 12 and the steerable portion 124. This extension apparatus 128 allows the operator one more tool to carefully adjust the position of the guidewire construct 120 within a vessel such as the aorta so the sail can be positioned to direct the guidewire into a desired direction of blood flow. The distal portion 122 of the guidewire may be extended from the steerable portion 124 independent of the state of the steerable portion, whether it is flexed or straight.

Figure 23:
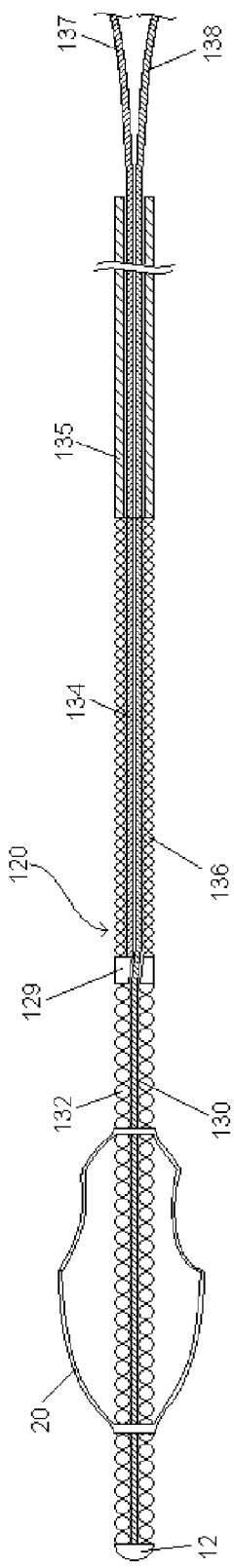
FIG. 23 is an enlarged longitudinal sectional view of the steerable guidewire with a mounted sail and an extendable distal portion of FIG. 22.

FIG. 23 shows the structure of a guidewire embodiment with steering and extension features. In FIG. 23, the guidewire 120 has a distal portion which consists of a distal tip 12, an extension wire 130 and a distal coil 132. The steering portion of the guidewire consists of a coil 136 (or flexible tube) and two wires, a steering wire 134 and the extension wire 130. The steering wire 134 and the extension wire 130 extend proximally through the proximal tube 135 and out of the proximal end of the catheter with the steering wire 134 having a proximal end 137 and the extension wire 130 having a proximal end 138. To flex or steer the catheter, the proximal end 137 of the steering wire 134 is moved relative to the proximal tube 135. This can direct the distal portion of the guidewire in a desired direction. To extend or retract the distal portion of the catheter, the proximal end 138 of the extension wire 130 is advanced or retracted relative to the proximal tube 135. The steering wire 134 is joined to the linking member 129. The linking member 129 has an orifice through it which the extension wire 130 passes. The extension wire 130 is bonded to the distal tip of the catheter 12 as is the distal coil 132. When the extension wire 130 is advanced relative to the proximal tube 135, the distal coil, sail, and distal tip are extended as is shown in FIG. 22. The proximal end of the distal coil 132 may have a ring or band to hold the coil in place. The operator may control the steering and advancement by a simple apparatus such as that shown in FIGS. 17a and 17b with the apparatus being adapted to adjust two wires independently.

Figure 24:
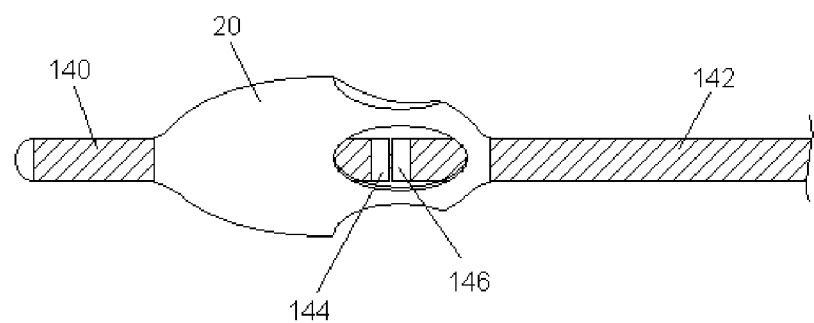
FIG. 24 is an enlarged isometric view of a portion of a guidewire with a sail mounted near its tip with a distal portion that may extend distally.
Figure 25:
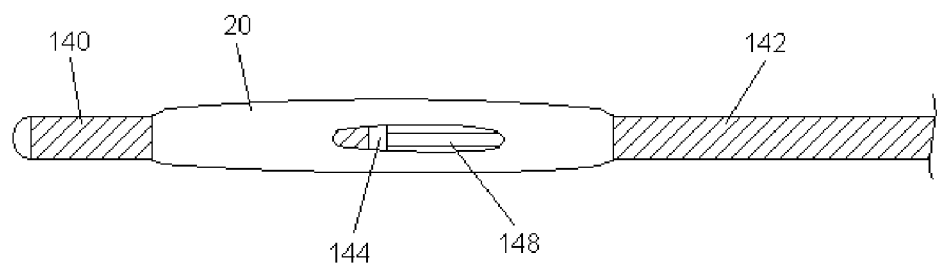
FIG. 25 is an enlarged isometric view of the guidewire of FIG. 24 with a sail mounted near its tip with a distal portion that is extend distally.

In another preferred embodiment, the guidewire with an incorporated sail may have design features which allow for the sail to be collapsed against the guidewire or catheter regardless of the flow in the vessel which the sail is positioned. FIGS. 24 to 27 depict embodiments of the technology where the operator can actively collapse the sail against the guidewire. Shown in FIG. 24 is a guidewire with a proximal portion 142 and a distal portion 140 with a sail 20 which is attached to both the proximal portion 142 with a distal portion 140. There is a proximal joint end 146 and a distal joint end 144. FIG. 25 shows the same guidewire as FIG. 24 except the distal portion 140 has been extended out from the proximal portion 142 as a shaft 148 is advanced through the proximal portion 142. The sail 20 has been elongated and therefore its diameter has been reduced to nearly that of the proximal 142 and distal 140 portions of the guidewire. The shaft 148 can be advanced by the operator at the proximal end of the guidewire to collapse the sail. This feature may be useful to minimize the potential of the sail becoming caught on a stent or other intravascular structure during removal of the guidewire or catheter.

Figure 26:
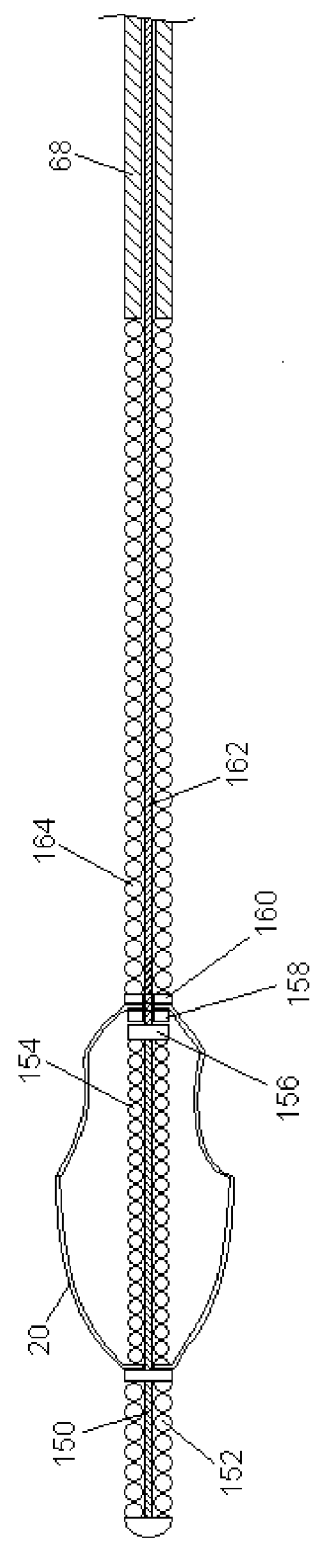
FIG. 26 is an enlarged longitudinal sectional view of a portion of a guidewire with a sail mounted near its tip with a distal portion that may extend distally.
Figure 27:
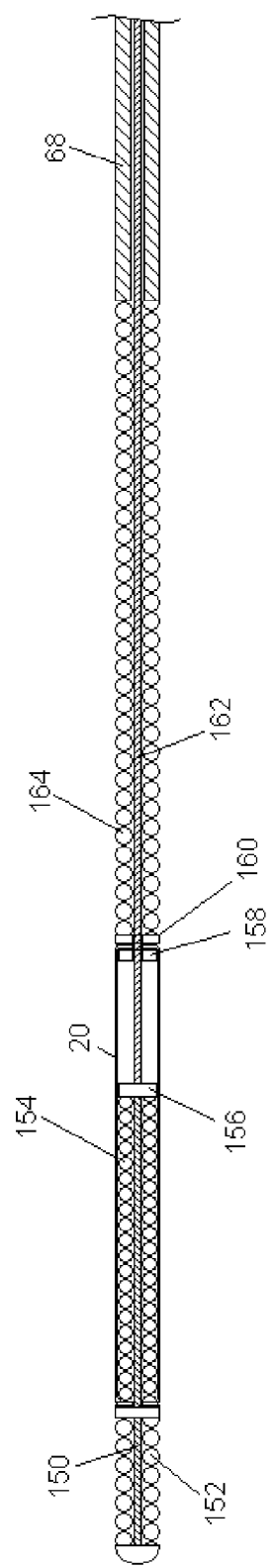
FIG. 27 is an enlarged longitudinal sectional view of the guidewire of FIG. 26 with a sail mounted near its tip with a distal portion that is extended distally.

FIG. 26 is a cross-section of an embodiment where different portions of the guidewire have different diameters where, when the sail is collapsed against the guidewire, the diameter of the complete device is uniform. In description, the guidewire is constructed of traditional design in its distal portion with a core wire 152 surrounded by coils of wire of differing diameter with a tip coil 152 and a sail coil 154 in the area of the sail 20. The core wire 150 is bonded or attached to the distal end plate 156. The proximal portion of the guidewire has a shaft 162 which extends through the proximal tubing 68 and proximal coil 164. The shaft 162 extends through two hollow cylinders 158 and 160 which together sandwich the sail 20. The shaft is then attached to the distal end plate 156. Advancement of the shaft 162 in the distal direction will extend the distal end plate 156 as well as the sail coil 154, the core wire 152 and the tip coil 150. This will result in the sail being collapsed against the guidewire as shown in FIG. 27. As seen in FIG. 27, since the sail coil 154 is of a smaller diameter than the tip coil 152 and the proximal coil 164 when the sail 20 is in a collapsed position the diameter of the sail section is equal to or less than the adjacent sections of the guidewire, although it may be slightly greater in diameter for some applications.

Figure 28:
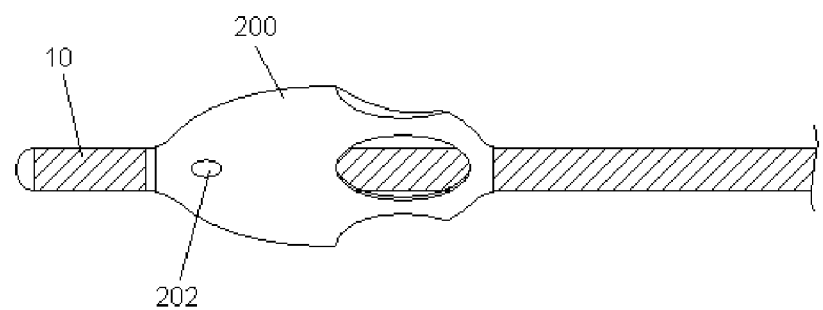
FIG. 28 is an enlarged isometric view of a guidewire with a sail mounted near its tip with a distal hole in the sail.

FIG. 28 is another preferred embodiment where a guidewire 10 has a sail 200 attached to it with an opening 202 in the distal aspect of the sail. This distal hole(s) 202 in the sail 200 may be useful in a number of clinical scenarios. If the sail is entering a stenosis and has occluded the opening of the stenosis there will be no flow through the stenosis until the entire sail has passed the stenosis. If the clinician would like an angiographic image of the vessel there must be flow in it. The distal hole would allow some flow through the stenosis and may allow the clinician to obtain an angiographic image of the vessel while the sail is in the stenosis. If the sail is used in a small vessel, the diameter of the sail in the extended position may be larger than the diameter of the vessel. Since the sail is so thin and flexible, it may be safely advanced up such vessel and possibly even through a stenosis in that vessel. The distal hole would allow flow and possible angiographic evaluation of that vessel with the sail in it. The distal openings may also promote the advancement of the guidewire through a lesion by allowing some flow to continue through the lesion even when the guidewire and sail are within the lesion and the sail is partially collapsed. These distal openings may also facilitate the smooth collapse of the sail against the guidewire. The distal opening(s) may be optimized in number, shape and location to facilitate efficient collapse and perhaps also folding of the sail on the guidewire. These distal openings may also stabilize the sail in the presence of flow and smoothly direct it into the area of maximum flow. The distal opening(s) may also serve to improve the opening of the sail in the presence of flow. If the sail is constructed of thin and flexible material, it may collapse, even with gravitational force. The distal holes in the catheter may facilitate flow through the catheter and improve the opening of the sail and contribute to keeping it open in the presence of flow. Additionally, these distal openings may also stabilize the sail in the presence of flow and smoothly direct it into the area of maximum flow. The distal openings may not be holes where material has been removed from the sail rather they may only be cuts, incisions, or otherwise separations in a portion of the sail. These controlled separations may realize the above stated potential benefits in a manner similar to holes. The distal openings may have a total cross-sectional area which is smaller than the cross-sectional area of the proximal opening(s) so the sail imparts drag force to the guidewire.

Figure 29:
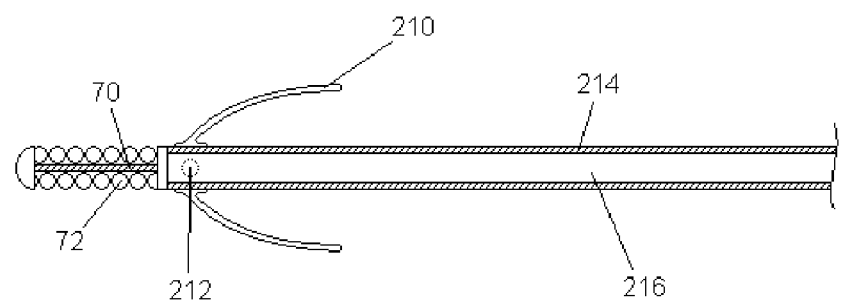
FIG. 29 is an enlarged longitudinal sectional view of a guidewire with a balloon expandable sail mounted near its tip.

The sail may be inflatable and collapsible. FIG. 29 depicts a guidewire with a proximal tube 214 with lumen 216 attached to distal core wire 70 and distal coil 72. The tubing may have one or more openings 212 at or near its distal end with a balloon 210 positioned over the opening and sealed to the tubing 214 such that fluid or gas passed through the tubing lumen 216 would inflate the balloon. The balloon may be of shape that a useful amount of drag is transmitted to the guidewire or catheter in the presence of flow in a vessel, duct or lumen which it is within. After the sail has assisted the guidewire or catheter into the desired position, a vacuum applied to the tubing 216 will deflate the balloon 210 and allow the guidewire or catheter to be removed from the vessel, duct or lumen or simply for unimpeded flow to resume.

Figure 30:
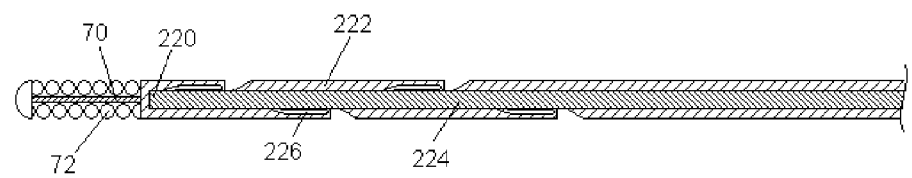
FIG. 30 is an enlarged longitudinal sectional view of a guidewire or catheter with multiple extendable sails mounted near its tip with sails in the retracted position.
Figure 31:
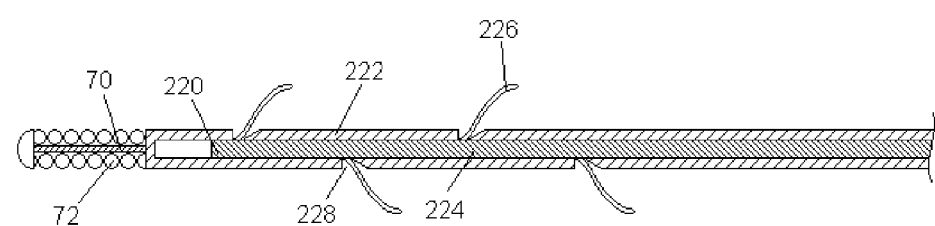
FIG. 31 is an enlarged longitudinal sectional view of the guidewire or catheter of FIG. 30 with multiple extendable sails mounted near its tip with sails in the extended position.

In another preferred embodiment, a guidewire or catheter may have sails which can extend from the device and retract back into the device. For completeness, the sails may begin in an extended position and only be retracted back into the device or they may be able to extend from within the device and then be retracted back in and finally they may be able to be extended from within the device and not retracted back into the device. Shown in FIG. 30 is an embodiment where a catheter or guidewire has a proximal tube 222 and a distal traditional guidewire portion with a core wire 70 and distal wire coil 72. Within the proximal tube 222 is a shaft 224 with a distal end 220 and one or more individual sails 226 mounted to the shaft 224. These sails 226 are non-circumferential. In this position, the sails 226 are in a retracted position and do not extend beyond the diameter of the proximal tube 222. As shown in FIG. 31, when the shaft 224 with distal tip 220 is moved proximally with respect to the proximal tube 222, the sails 226 are moved proximally and extend out of the proximal tube 222 through openings 228 in it. The sails 226 are now in an extended position and may impart drag to the catheter or guidewire in the presence of flow. If the shaft 224 is advanced distally with respect to the outer tube 222 the sails 226 will retract and no longer be outside the outer tube 222. There may be one single sail or one or more sails only on one side or portion of the guidewire or catheter. This may allow the user to effectively steer the guidewire by manipulation of the extension or retraction of the sail or the number of sails extended or retraction and their position within, upon or about the guidewire or catheter. There may be more than one shaft and it is conceived any degree of complexity of arrangements to provide the user any desired flexibility in directing this device into a desired location. This may resemble the control of a sailboat with multiple sails, their direction and degree of extension to direct a boat in a desired direction, even if the direction is not simply in the direction of the wind. A modification of this embodiment may also have clinical utility. There may be openings between the tube and the guidewire portion or there may be no guidewire portion. This would allow fluid to flow from the tube into a vessel duct or lumen at or near the distal aspect of the catheter. Additionally, the shaft could be smaller than the lumen of the tube or proximal tube or the shaft itself could be a tube such that fluid could flow through the device. With these or similar modifications applied to this or other embodiments herein this device may be able to be directed to a desired area (with or without steering features) do deliver a fluid, solid or any combination or intermediary thereof (i.e., drug, gas or other biologically active agent, compound, molecule or other matter) within the body of a living being. This delivered fluid or other matter may have a therapeutic benefit for the patient.

Figure 32:
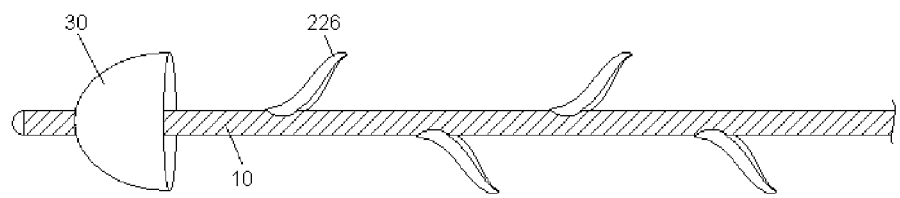
FIG. 32 is an enlarged isometric view of a portion of a guidewire with a sail mounted near its tip with multiple non-circumferential sails mounted more proximal on the guidewire.

FIG. 32 is another preferred embodiment where one or more non-circumferential sails 226 and one or more circumferential sails 30 are mounted to the same guidewire 10. The combination of sail designs may enhance the performance of the device. The non-circumferential sails 226 may be proximal, distal or a combination of proximal and distal to with respect to the circumferential sails and their location on the guidewire 10 or catheter. The non-circumferential sails may be able to be advanced or retracted. One or more of the non-circumferential sails may be positioned as to provide non-uniform or asymmetric drag to the guidewire or catheter such that in the presence of flow the distal tip of the guidewire or catheter is directed according to this differential drag on the guidewire. This may be used to select a vessel, duct or lumen for the guidewire to enter. This may be another means of steering the guidewire.

Figure 33:
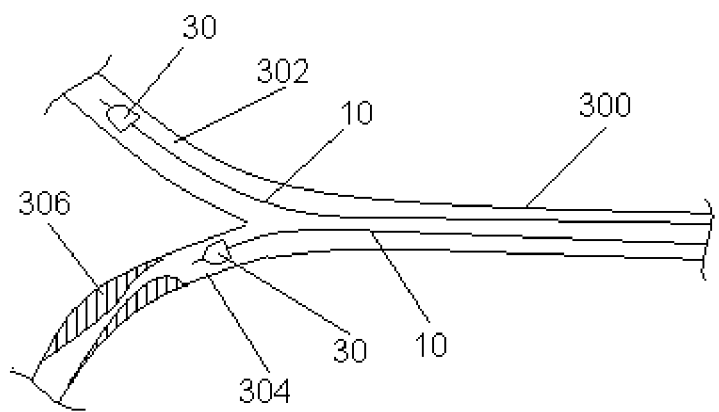
FIG. 33 is a view of a vessel with two branches and two guidewires each guidewire with sails mounted near the tips partially in section.

In order for the guidewire with the flow directed sail to be aided by drag forces, flow must be present in the vessel. In some vessels there may be lower flow secondary to a stenosis, especially if that stenosis is near a branch in the vessel and another branch has no obstruction. Such a described situation is shown in FIG. 33. A vessel 300 has a non-stenosed branch 302 and a stenosed branch 304 with a stenosis 306. Two sail mounted guidewires are within the vessel 300 with guidewires 10 and sails 30. One guidewire is extended into the non-stenosed branch 302 and one into the stenosed branch 304. By placing a sail 30 mounted to a guidewire 10 in the non-stenosed branch 302, it effectively limits the cross-sectional area of that branch, thus increasing resistance and reducing blood flow through this branch. This provides increased flow in the branch 304 relative to before the branch 302 was partially occluded and improves the ease at which a sail directed guidewire may be advanced into branch 304 and if desired through the lesion 306. This is another application of the technology and may also be an effective method for selecting a vessel for the catheter or guidewire to enter. This may be used in non-diseased vessels also. If a sail directed guidewire repeatedly guides itself into an undesired branch, that guidewire may be left there to limit flow in that vessel and a second sail directed guidewire can be used which will then be guided into the other branch. An angioplasty balloon or other device could be used to block flow in a vessel but the thin flexible sail may be less traumatic and easier to manipulate.

Preliminary testing has been done to demonstrate the utility of this technology. Similar to the device shown in FIG. 2, sails constructed of silicon were formed by dip coating a cylinder with a rounded tip. Once the silicon had cured, a sail was removed and mounted to a traditional guidewire with a diameter of 0.014 inches (360 microns) just millimeters from the distal tip. The sail was adhered to the guidewire with a small amount of adhesive. A model of a stenosed vessel was created using a flexible silicon cured within a 4.7 mm internal diameter tube with a 0.062 inch (1.6 mm) or 0.035 inch (0.89 mm) diameter tube eccentrically placed tube within it. Once the silicon was cured, a very eccentric 65% or 81% stenosis was created within the vessel. The vessel was placed in a circuit with continuous flow at 100 ml/min using a roller pump. A hemostasis valve was present in the circuit proximal to the lesion to allow the introduction of guidewires into the circuit. A traditional guidewire was positioned within the tubing with the stenosis and a trained vascular surgeon with extensive endovascular interventional experience was not able to direct the guidewire through the eccentric lesion in two minutes under direct vision. The result is depicted in FIG. 4. A guidewire with a sail (diameter of approximately 0.045 inches (approx. 1.1 mm) in expanded position) was then advanced into the vessel with the stenosis and as the tip of the guidewire approached the stenosis (depicted in FIG. 5) the sail was directed from the center of the lesion laterally toward and into the eccentrically located stenosis and the guidewire was easily advanced through the stenosis as is depicted in FIG. 6. This required no manipulation of the guidewire, just gentle advancement. This was repeated numerous times with different sails and guidewires and the outcome was the same. This device will save time in the cath lab by simplifying the most complicated maneuver in interventional cardiology and reducing the time needed to treat each patient. This will allow more patients to be treated in a single cath lab in a day than without this technology. This technology may also allow patients to be treated who otherwise may not be attempted to be treated or successfully treated given the complexity of their disease.

In accordance with another aspect of this invention, the catheter or guidewire with one or more sail constructs could also have additional features such as a dilating or angioplasty balloon, lubricous coating, drug or active biological compound release, distal protection filters, or embolization technology. A guidewire or catheter with a mounted sail may need an introducer tube to be removably advanced through a sheath valve or Tuohy Borst valve and the guidewire or catheter advanced through the introducer tube to protect the integrity of the sail(s).

It should be understood that the foregoing disclosure and description of the present invention are illustrative and explanatory thereof and various changes in the size, shape, and material composition, as well as in the description of the preferred embodiment, may be made without departing from the spirit of the invention.

What is claimed is:

1. A device for accessing a vessel, duct or lumen, comprising a guidewire or catheter having a proximal end and a distal end, and at least one projection attached said guidewire or catheter at the distal end of the guidewire or catheter, wherein said at least one projection is configured to be controllably extended and retracted by an operator of said device, and wherein said at least one projection is configured to be held in an expanded configuration by flow within the vessel, duct, or lumen to impart an asymmetric drag on said guidewire such that said guidewire is thereby rendered steerable within the vessel, duct, or lumen.

2. The device of claim 1, wherein at least one portion of said guidewire or catheter is flexed under control of an operator, thereby angling a distal portion of said guidewire or catheter within said vessel, and further wherein said projection is distal to said flexed portion of the guidewire or catheter.

3. The device of claim 2, further comprising an expansion proximal to the flexed portion of the guidewire or catheter.

4. The device of claim 3, wherein said expansion imparts more drag force to the guidewire or catheter when flow within said vessel, duct, or lumen is from a proximal to distal direction than when flow is from a distal to proximal direction.

5. The device of claim 2, further comprising an extension apparatus which permits the operator to increase a distance between the distal end of the guidewire or catheter and the flexed portion of the guidewire or catheter.

6. The device of claim 1, wherein said guidewire or catheter is flexible.

7. The device of claim 1, wherein said at least one projection comprises a sail comprising a flexible sheet material.

8. The device of claim 7, wherein said flexible sheet material comprises at least one polymer material.

9. The device of claim 7, wherein said flexible sheet material comprises at least one reinforcement material.

10. The device of claim 9, wherein said reinforcement material comprises at least one of integrated fibers and wires.

11. The device of claim 7, wherein said sail is collapsible against said guidewire or catheter.

12. The device of claim 11, wherein said sail is collapsible upon an operator manipulating a control mechanism at said proximal end of said device.

13. The device of claim 11, wherein said sail is collapsible upon at least one of (i) contact with a stenosis and (ii) application of an axial force from a proximal aspect of said guidewire or catheter.

14. The device of claim 7, wherein said sail is attached to said guidewire or catheter by at least one technique selected from the group consisting of (i) adhesive bonding and (ii) a mechanical attachment.

15. The device of claim 14, wherein said mechanical attachment comprises a friction fit.

16. The device of claim 15, wherein said friction fit comprises a clamping action.

17. The device of claim 1, further comprising a crossing profile not greater than 0.016 inches.

18. The device of claim 1, wherein said at least one projection is arranged to collapse against said guidewire or catheter in a proximal direction.

19. The device of claim 1, wherein said at least one projection is arranged to evert or turn inside-out and collapse against said guidewire or catheter in a distal direction.

20. The device of claim 1, wherein said at least one projection is arranged symmetrically radially about said guidewire or catheter.

21. The device of claim 1, wherein said at least one projection is arranged radially asymmetrically about said guidewire or catheter.

22. The device of claim 1, wherein said at least one projection is controllably extended in a manner that is asymmetric about a longitudinal axis of said guidewire or catheter, thereby causing an asymmetric drag on said guidewire or catheter.

23. The device of claim 1, wherein a diameter of said guidewire or catheter at said projection is smaller than a diameter elsewhere along said guidewire or catheter.

24. The device of claim 1, further comprising at least one opening in a proximal portion of said projection.

25. The device of claim 1, wherein a distal-most aspect of said projection is within 2 cm of said distal end of said guidewire or catheter.

26. The device of claim 1, wherein a distal-most aspect of said projection is within 1 cm of said distal end of said guidewire or catheter.

27. The device of claim 1, wherein said projection comprises a sail that the operator controllably inflates and collapses.

28. The device of claim 27, wherein said guidewire or catheter comprises a tube defining a second lumen in communication with a source of fluid or gas, and said sail is positioned over an opening in said tube, and sealed to said tube such that said second lumen furthermore is in communication with said sail.

29. The device of claim 1, wherein said asymmetric drag on said guidewire or catheter is also sufficient to pull said guidewire or catheter along with the flow.

30. A device for accessing a vessel, duct or lumen, comprising a guidewire or catheter having a proximal portion and a distal portion, and at least one operably advancing and retracting sail mounted at the distal portion of the guidewire or catheter, wherein said at least one sail is configured to be held in an advanced position by flow within the vessel, duct, or lumen to impart a non-uniform drag on said guidewire or catheter, thereby rendering said guidewire or catheter steerable within the vessel, duct, or lumen.

31. A device for accessing a vessel, duct or lumen in the presence of flow therein, comprising:
  (a) a guidewire or catheter having a proximal portion and a distal portion; and
  (b) at least one non-circumferential sail mounted to said distal portion, wherein said at least one non-circumferential sail is configured to be controllably advanced and retracted, and wherein said at least one non-circumferential sail is positioned to provide a degree of differential drag on said guidewire or catheter in the presence of flow, thereby rending said guidewire or catheter steerable within the vessel, duct, or lumen.

32. The device of claim 31, whereby a distal tip of said guidewire or catheter is directed according to said differential drag.

33. The device of claim 31, wherein said non-circumferential sail comprises a sail mounted only to one side of said guidewire or catheter.

34. The device of claim 31, whereby said controllably advanced and retracted non-circumferential sail is controlled by a user of said device.

35. The device of claim 31, wherein said non-circumferential sail is advanced and retracted by means of a shaft controllably moved distally and proximally.

36. The device of claim 35, wherein said shaft is mounted within a lumen defined by said guidewire or catheter.

37. The device of claim 31, further comprising at least one circumferential sail mounted to said guidewire or catheter.

38. The device of claim 37, wherein said circumferential sail has a proximal aspect and a distal aspect, and further wherein said circumferential sail comprises at least one opening on said proximal aspect.

39. The device of claim 38, wherein said circumferential sail further comprises at least one opening on said distal aspect.

40. The device of claim 39, wherein a total area of said distal aspect opening is less than a total area of said proximal aspect opening.

41. The device of claim 37, wherein said circumferential sail comprises at least a portion of an ellipsoid shape, with a major axis of the ellipsoid being coaxial with said guidewire or catheter.

* * * * *